US005578493A

United States Patent [19]
Gilliam et al.

[11] Patent Number: 5,578,493
[45] Date of Patent: Nov. 26, 1996

[54] WILSON'S DISEASE GENE

[75] Inventors: T. Conrad Gilliam, New York, N.Y.; Rudolph E. Tanzi, Canton, Mass.

[73] Assignees: The Trustees of Columbia University in the City of New York, New York, N.Y.; General Hospital Corporation, Boston, Mass.

[21] Appl. No.: 118,441

[22] Filed: Sep. 1, 1993

[51] Int. Cl.[6] .......................... C07H 21/00; C12N 9/00; C12N 15/12; C12N 15/63

[52] U.S. Cl. .................................. 435/320.1; 435/172.3; 435/183; 435/196; 536/23.5; 536/24.31; 935/23; 935/24; 935/29; 935/9

[58] Field of Search .......................... 514/44; 536/23.1, 536/23.2, 23.5; 435/320.1, 172.3, 183, 196; 935/23, 24, 29, 9

[56] References Cited

PUBLICATIONS

Kooy et al. 1993 Human Genetics 91:504–506.
Vulpe et al. 1993. Nature Genetics 3:7–13.
Chelly et al. 1993. Nature Genetics 3:14–19.
Mercer et al. 1993. Nature Genetics 3:20–25.
Chelly et al. 1993. Nature Genetis 5:317–318.
Bull et al. 1993 Nature Genetics 5:327–337.
Petrukhin et al. 1993. Nature Genetics 5:338–343.
Tanzi et al. 1993. Nature Genetics 5:344–350.
Yamaguchi et al. 1993. Biochem. Biophys. Res. Comm. 197(1):271–277.
Watson, 1993. Tibtech 11:114–117.

Primary Examiner—Jasemine C. Chambers
Assistant Examiner—Brian R. Stanton
Attorney, Agent, or Firm—John P. White

[57] ABSTRACT

This invention provides an isolated, vertebrate nucleic acid molecule encoding the normal protein that prevents development of Wilson's disease. This invention also provides a nucleic acid molecule comprising a nucleic acid molecule of at least 15 nucleotides capable of specifically hybridizing with a sequence included within the sequence of the above-described nucleic acid molecule. Finally, this invention provides various uses of the isolated Wilson's disease gene.

12 Claims, 20 Drawing Sheets

FIGURE 2A FIGURE 2B FIGURE 2C
 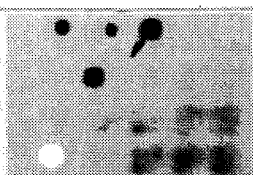 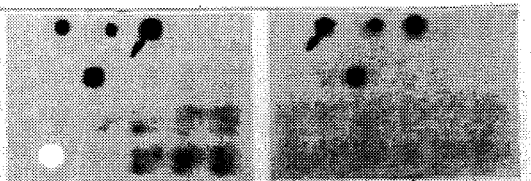
A. Probe: 3a3 (arrow)  B. Probe: 3a4 (arrow)  C. Probe: 2a2 (arrow)
Positives: 3a4,2a2,5b3  Positives: 3a3,2a2,5b3  Positives: 3a3,3a4,5b3
FIGURE 2D FIGURE 2E FIGURE 2F
  
D. Probe: 5b3 (arrow)  E. Probe: 4b2 (arrow)  F. Probe: 4b4 (arrow)
Positives: 3a3,3a4,2a2,4b2  Positives: 5b3, 4b4  Positives: 4b2, 5a5
FIGURE 2G
G. Probe: 5a5 (arrow)
Positive: 4b4
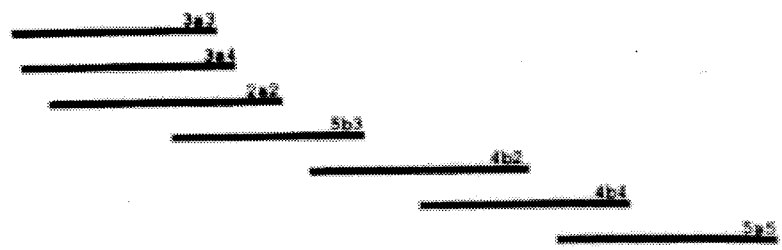

FIGURE 5A

```
1                                                  GTGGAGGGCATGACC
                                                   | V  E  G  M  T |   5
16  TGCCAGTCCTGTGTCAGCTTCCATTGAAGGCAAGGTCCGGAAACTGCAAGGA
    | C  Q  S  C  V  S  S  I  E  G  K  V  R  K  L  Q  G |  22
67  GTAGTGAGAGTCAAAGTCTCACTCAGCAACCAAGAGGCCGTCATCACTTAT
    | V  V  R  V  K  V  S  L  S  N  Q  E  A  V  I  T  Y |  39
118 CAGCCTTATCTCATTCAGCCCGAAGACCTCAGGGACCATGTAAATGACATG
    | Q  P  Y  L  I  Q  P  E  D  L  R  D  H  V  N  D  M |  56
169 GGATTTGAAGCTGCCATCAAGAGCAAAGTGGCTCCCTTAAGCCTGGGACCA
    | G  F  E  A  A  I  K  S  K  V  A  P  L  S  L  G  P |  73
220 ATTGATATTGAGCGGGTTACAAAGCACTAACCCAAAGACCTTTATCTTCT
    | I  D  I  E  R  L  Q  S  T  N  P  K  R  P  L  S  S |  90
271 GCTAACCAGAATTTTAATAATTCTGAGACCCTTGGGGCACCAAGAAGCCAT
    | A  N  Q  N  F  N  N  S  E  T  L  G  H  Q  G  S  H |  107
322 GTGGTCACCCTCCAACTGAGAATAGATGGGAATGCATTGTAAGTCTTGCGTC
    | V  V  T  L  Q  L  R | I  D  G  M  H  C  K  S  C  V |  124
373 TTGAATATTGAAGAAAATATTGGCCAGCTCCTAGGGTTCAAAGTATTCAA
    | L  N  I  E  E  N  I  G  Q  L  L  G  V  Q  S  I  Q |  141
424 GTGTCCTTGGAGAACAAAACTGCCCAAGTAAAGTATGACCCTTCTTGTACC
    | V  S  L  E  N  K  T  A  Q  V  K  Y  D  P  S  C  T |  158
475 AGCCCAGTGGCTCTGCAGAGGGCTATCGAGGCACTTCCACCTGGAATTTT
    | S  P  V  A  L  Q  R  A  I  E  A  L  P  P  G  N  F |  175
```

FIGURE 5B

```
526  AAAGTTTCTCTTCCTGATGGAGCCGAAGGGAGTGGGACAGATCACAGGTCT   192
      K  V  S  L  P  D  G  A  E  G  S  G  T  D  H  R  S
577  TCCAGTTCTCATTCCCCTGGCCACCGAGAAACCAGGTCCAGGGCACA     209
      S  S  H  S  P  G  S  P  P  R  N  Q  V  Q  T
628  TGCAGTACCACTCTGATTGCCGGCATGACCTGTGCATCCTGTGTC       226
      C  S  T  T  L  I  A  G  M  T  C  A  S  C  V
679  CATTCCATTGAAGGCATGATCTCCCAACTGGAAGGGGTGCAGCAAATATCG 243
      H  S  I  E  G  M  I  S  Q  L  E  G  V  Q  Q  I  S
730  GTGTCTTTGGCCGAAGGGACTGCAACTGTTCTTTATAATCCCTGTAATT   260
      V  S  L  A  E  G  T  A  T  V  L  Y  N  P  V  I
781  AGCCCAGAAGAACTCAGAGCTGCTATAGAAGACATGGGATTTGAGGCTTCA 277
      S  P  E  E  L  R  A  A  I  E  D  M  G  F  E  A  S
832  GTCGTTTCTGAAAGCTGTTCTACTAACCCTCTTGGAAACCACAGTGCTGGG 294
      V  V  S  E  S  C  S  T  N  P  L  G  N  H  S  A  G
883  AATTCCATGGTGCAAACTACAGATGGTACACCTACATCTGTGCAGGAAGTG 311
      N  S  M  V  Q  T  T  D  G  T  P  T  S  V  Q  E  V
934  GCTCCCACACTGGGAGGCCTCCCTGCAAACCATGCCCCGGACATCTTGGCA 328
      A  P  H  T  G  R  L  P  A  N  H  A  P  D  I  L  A
985  AAGTCCCCACAATCAACCCGAGCAGTGGCACCGCAGAAGTGCTTCTTACAG 345
      K  S  P  Q  S  T  R  A  V  A  P  Q  K  C  F  L  Q
1036 ATCAAAGGCATGACCTGTGCATCCTGTGTCTAACATAGAAAGGAATCTG  362
      I  K  G  M  T  C  A  S  C  V  S  N  I  E  R  N  L
```

FIGURE 5C

```
1087 CAGAAAGAAGCTGGTTCTCTCCGTGTTGGTTGCCTTGATGGCAGGAAAG
       Q  K  E  A  G  V  L  S  V  L  V  A  L  M  A  G  K    379
1138 GCAGAGATCAAGTATGACCCAGAGGTCATCCAGCCCCTCGAGATAGCTCAG
       A  E  I  K  Y  D  P  E  V  I  Q  P  L  E  I  A  Q    396
1189 TTCATCCAGGACCTGGGTTTTGAGGCAGCAGTCATGGAGGACTACGCAGGC
       F  I  Q  D  L  G  F  E  A  A  V  M  E  D  Y  A  G    413
1240 TCCGATGGCAACATTGAGCTGACAACAGGGATGACCTGCGCGTCCTGT
       S  D  G  N  I  E  L  T  I  T  G  M  T  C  A  S  C    430
1291 GTCCACAACATAGAGTCCAAACTCAGGACAAATGGCATCACTTATGCC
       V  H  N  I  E  S  K  L  R  T  N  G  I  T  Y  A       447
1342 TCCGTTGCCCTGGCCACCAGCAAAGCCCTTGTTAAGTTTGACCCGGAAATT
       S  V  A  L  A  T  S  K  A  L  V  K  F  D  P  E  I    464
1393 ATCGGTCCACGGGATATTATCAAAATTATTGAGAGAAACCTCAGAAGCC
       I  G  P  R  D  I  I  K  I  I  E  S  K  T  S  E  A    481
1444 CTGGCTAAACTCATGTCTCTCCAAGCCACAGAAGCCACCGTTGTGACCCTT
       L  A  K  L  M  S  L  Q  A  T  E  A  T  V  V  T  L    498
1495 GGTGAGGACAATTTAATCATCAGGGAGGAGCAAGTCCCCATGGAGCTGGTG
       G  E  D  N  L  I  I  R  E  E  Q  V  P  M  E  L  V    515
1546 CAGCGGGGCGATATCGTCAAGGTGGTTCCTGGGGGAAAGTTTCCAGTGGAT
       Q  R  G  D  I  V  K  V  V  P  G  G  K  F  P  V  D    532
1597 GGGAAAGTCCTGGAAGGCAATACCATGGCTGATGAGTCCCTCATCACAGGA
       G  K  V  L  E  G  N  T  M  A  D  E  S  L  I  T  G    549
```

FIGURE 5D

```
1648 GAAGCCATGCCAGTCACTAAGAAACCCGGAAGCACTGTAATTGCGAGGTCT
      E  A  M  P  V  T  K  K  P  G  S  T  V  I  A  R  S   566
1699 ATAAATGCACATGGCTCTGTGCTCATTAAAGCTACCCACGTGGGCAATGAC
      I  N  A  H  G  S  V  L  I  K  A  T  H  V  G  N  D   583
1750 ACCACTTTGGCTCAGATTGTGAAACTGGTGGAAGAGGCTCAGATGTCAAAG
      T  T  L  A  Q  I  V  K  L  V  E  E  A  Q  M  S  K   600
1801 AACCCCAACAAGCACATCTCCCAGACAGAGGTGATCATCCGGTTTGCTTTC
      N  P  N  K  H  I  S  Q  T  E  V  I  I  R  F  A  F   617
1852 CAGAGTCCATCACGGGTGCTGTGCATTGGTGCCCCCTGGGCTG
      Q  S  L  T  R  V  L  C  I  G  A  C  P  C  S  G  L   634
1903 GCCACGCGCCCCATGGTGTCAGAGCCGGTGGCCGCGAACGGC
      A  T  R  P  M  V  S  E  P  V  A  A  Q  N  G         651
1954 ATCCCTCATCAAGGAGGCAAGCCCCTGGAGATGGCCCACAAGATAAAGACT
      I  P  H  Q  G  G  K  P  L  E  M  A  H  K  I  K  T   668
2005 GTGATGTTTGACAAGACTGGGACTATCACCCACGGTGTCCCCAGGGTCATG
      V  M  F  D  K  T  G  T  I  T  H  G  V  P  R  V  M   685
2056 CGGGTGCTCCTGCTGGGAGATGTGGCCACACTGCCCCTCAGGAAGGTTCTG
      R  V  L  L  L  G  D  V  A  T  L  P  L  R  K  V  L   702
2107 GCTGTGGTGGGGACTGCGGAGGCCAGTGAGCATCCCCTTGGGGTGGCA
      A  V  V  G  T  A  E  A  S  E  H  P  L  G  V  A     719
2158 GTCACCAAAATACTGTAAAGAGGAACTTGGAAGAGACCTTTGGGATACTGC
```

FIGURE 5E

```
        V   T   K   Y   C   K   E   E   L   G   T   E   T   L   G   Y   C        736
2209  ACGGACTTCCAGGCTGTGGAATTGGGCACAGAAACTCTTGGCTACTGCAAC
        T   D   F   Q   A   V   P   G   C   G   I   G   C   K   V   S   N        753
2260  GTGGAAGGCATCCTGGCCCACGTGAGCGCCTTTGATGTGCCCGGCCAGT
        V   E   G   I   L   A   H   S   E   R   P   L   S   A   P   A   S        770
2311  CACCTGAATGAAGCCTGGCCAGCCTTCCCAGAAAAGATGCTGTCCCCCAG
        H   L   N   E   A   G   S   L   P   A   E   K   D   A   V   P   Q        787
2362  ACCTTTCTGTGCTGATTGGGAACCGTGAGGCAACGGTTTA
        T   F   S   V   L   I   G   N   R   E   W   L   R   N   G   L            804
2413  ACCATTTCTAGCGATGTCAGCGACGCCATGACAGACCACGAGATGAAAGGA
        T   I   S   S   D   V   S   D   A   M   T   D   H   E   M   K   G        821
2464  CAGACAGCAGCCATCCTGGTGGCTATTGACGGTGTGCTCTGTGGGATGATCGCA
        Q   T   A   I   L   V   A   I   D   G   V   L   C   G   M   I   A        838
2515  ATCGCAGACGCTGTCAAGCAGGAGGCTGCCCTTGCTGTGCACACGCTGCAG
        I   A   D   A   V   K   Q   E   A   A   L   A   V   H   T   L   Q        855
2566  AGCATGGGTGTGGACGTGGTTCTGATCACGGAAGACAGCC
        S   M   G   V   D   V   V   L   I   T   G   D   N   R   K   T   A        872
2617  AGAGCTATTGCCAAGACAAAGTCTTTGCAGAGGTGCTG
        R   A   I   A   T   Q   V   G   I   N   K   V   F   A   E   V   L        889
2668  CCTTCGCACAAGGTGGCCAAGGTCCAGAGCTCAACATAAAGGGAAGAAA
        P   S   H   K   V   A   K   V   Q   E   L   Q   N   K   G   K   K        906
2719  GTCGCCATGGTGGGGGATGGTGTCAATGACTCCCCGGCCCTTGGCCCAGGCA
        V   A   M   V   G   D   G   V   N   D   S   P   A   L   A   Q   A        923
```

FIGURE 5F

```
2770 GACATGGGGTGTGGCCATTGGCACCGGATGTGGCCATCGAGGCAGCC
      D   M   G   V   A   I   G   T   D   V   A   I   E   A   A    940
2821 GACGTCGTCCTTATCAGAAATGATTTGCTAGTGGTAGCATTCAC
      D   V   V   L   I   R   N   D   L   L   D   V   V   A   S   I   H    957
2872 CTTTCCAAGAGGACTGTCCGAAGGCATACGCATTGGTCCTGGCACTG
      L   S   K   R   T   V   R   R   I   R   I   N   L   V   A   L    974
2923 ATTTATAACCTGGTTGGGATACCCAGCAGGTGTCTTCATGCCCATC
      I   Y   N   L   V   G   I   P   I   A   G   V   F   M   P   I    991
2974 GGCATTGTGCTGCAGCCCTGGATGGGCTCAGCGCCATGGCCCTCCTCT
      G   I   V   L   Q   P   W   M   G   S   A   M   A   A   S   S    1008
3025 GTGTCTGTGGTGCTCTCATCCCTGCAGCTCAAGTGCTATAAGAAGCCTGAC
      V   S   V   V   L   S   S   L   Q   L   K   C   Y   K   K   P   D    1025
3076 CTGGAGAGGTATGAGGCACAGGCCCACATGAAGCCCCTGACGGCA
      L   E   R   Y   E   A   Q   A   H   G   H   M   K   P   L   T   A    1042
3127 TCCCAGGTCAGTGTGCACATAGGCATGGATGACAGGATGGGACTCCCCC
      S   Q   V   S   V   H   I   G   M   D   D   R   W   R   D   S   P    1059
3178 AGGGCCACACCATGGGACCAAGTCAGCCAGGTGTCGCTGTCC
      R   A   T   P   W   D   Q   V   S   Y   V   S   Q   V   S   L   S    1076
3229 TCCCTGACGTCCGACAAGCCATCTCGGCACAGCGCAGACGACGATGAT
      S   L   T   S   D   K   P   S   R   H   S   A   A   D   D   D    1093
3280 GGGGACAAGTGGTCTCCTGCTCCTGAATGGCAGGGATGAGGAGCAGTACATC
```

FIGURE 5G

```
       G  D  K  W  S  L  L  L  N  G  R  D  E  E  Q  Y  I   1110
3331 TGATGACTTCAGGCAGGCGGCCGGGGCAGGACTTGCCTCCACTCACCAC
       *
3382 AAGCTGAGCAGGACAGCCAGCAGGATGGGCTGAGCTAGCCTTCCAGCTT
3433 TGGGGACTTCCGCTGGGTCTCCAGTATGTGGGCCCCTGCCCCTGCACGC
3484 GGCCCTTGTCTGCCCTCAGCTGGGCCTTGGCAGCGGCCCCTGCCCTG
3535 CCTCTTGCCTGGACTGTAGAAGGTCAGTCGAGAGGCCGTCAGCATGGGCTTTGTCTTGGACTCACAGACCTC
3586 CTTTGGCTGGACTGTAGAAGGTCAGTCGAGAGGCTGTGAAATGGAGAAACAGTTTCATCAG
3637 TGCTTTGGAGTATTTAGGATGACTGGGCCTGTCCAGAGAACTGCAGACCTCAGTTTCATCAG
3688 GACCAAAAAACCCTCACTCGATGTGTCTTTGCCTTGTCTGCTTTCTCGAGACTCACTGTCA
3739 GGGTCTTTCTCAGGTGTGTCTGCCTCTGCCCTGTTTGCTTTCTCTGGGACCCC
3790 TTTACCCTCAACCCCTGCTCTCAGGCGCTCAACATCATGTCCTGTTCAGTGTCCTTGTGGTC
3841 TCGTACGCAACCCCTGCTCTCAGGCGCTCAACATCATGTCCTGTGTCAGTGTCCTTGTGGTC
3892 CTCGCAACCCCTGCTCTCAGGCGCTCAACATCATGTCCTGTGTGGGACCAATGTCCTTGTGGTC
3943 TTTGCTAACCTGCTTTCAAGTTGAGGAGAGTTCTTTTTTTGTTGCTGATGACTCTGGAGTGCTTGCATTTCAG
3994 CTTGAACCTGCTTTCAAGTTGAGGAGAGTTCTTTTTTTGTTGCTGATGACTCTGGAGTGCTTGCATTTCAG
4045 TCTTCTTCAAGTTGAGGAGAGTTCTTTTTTTGTTGCTTAAAGCCCCCTTGCTTCTCCAT
4096 GGAGTGTGTTGGCTTTCTGACCTGAGCTTCGGGCTTCCCCAGCCTGTGGGGCTGGAGTGAGGG
4147 CCTCAGAGCTTCAGGACGTCCTTCCATATCCCGTACTCCCTGTGCCTGTGGTGCCTGTAGGT
4198 TCTCGCGATTCAGGACGTCCTTCCATATCCCGTACTCCCTGTGCCTGTGGTGCCTGTAGGT
4249 AAACGTTTGCCCCATGTGGGAAACGTATGTGTCCCCTGCACGGC
4300 CCAAGGGCTTCGTTTTCAGTCTTCTGACTCTGTCACCTGTCGGGGTTCAGTA
```

FIGURE 5H

```
4351 GAGAATTCAATTACTAGCGCCTGCCTTGTGTGGAGGAAATGGTAC
4402 TGCCCAAATAGGAGGAAAACACAGCCTCCCTGAGCCTGCATTCTGCACGCT
4453 GCCCAGGGCTTCAGAAAAGGAGGTGGCCACCCCGAAGGCACCCAGGAGCATCT
4504 ATTTACCTGGCAGTGGCTCTCAGAGCAGAACGGGTTCAGTTTTAGACT
4555 CTGAAGTTGGTTGTGATTGACAGAACCCTTTGGGAGCAAACTAGTAGAGTT
4606 GGATTAAATTCTGGGTGAAAACCCTTTCTCCACACAAAATAGTTTTAGTG
4657 ATTTTTTTCATTGTCCATTACTTGCCAGGGCAGTTTTAGCACTTTTG
4708 ATAGATTACGTCTAATCCTCCCAACACAGGGTAGCTATTACTGTC
4759 CACATTTTACAGGCAAGGACAAGCAGTTCCAAGAGGCTGAGGACTTTGCCCA
4810 GGATGACATAGCCAATGGACACTGTCTGTGATAAGAATAAACGA
4861 TCTTATTGTCCTTCTACCTTGAATAGAAGTTTTCCTACCAGGTGATCTATTCA
4912 GGAAAAAGGTCCTTGCCTGGAAATCAGGAGGTCATCTGACCTTCACCT
4963 TTGTTTCAACTCAGAATGCACTTTTTCACTTTCAGGGGTTTCAGCCCCTCCCGA
5014 TGGATGGTTAGTTCACGCGCTTGTGTTGATTGTGCTGTCCGTAATTGTGTCCGT
5065 TAAAATCCAGCCCGCACAGGAAATGTTTTTAAAACTTTATAGAAATAACGTTGTT
5116 CTCCAGCCCGCACACTAGGCAAATTGTGTCCGTAATTTATAGAAATAACGTTGTT
5167 TATGCTTGCTTGGGGAAATGTTTGATTTTGAAAATATTTATAGAAATAACGTTGTT
5218 GAATCTAATTCTGTTGATTTTGAAAATATTTATAGAAATCATTTCTACTTCAA
5269 CATATATGGACAGTGTAAGGAGTTTTTTGTCAGATAATCATTTCTACTTCAA
5320 GATGGTCAAAGTGTAAGGAGTTTTTTGTCAGATAATCATTTCTACTTCAA
5371 AAACATTTCATGCAAATATTAGAATAAAAGTTCCTGTCATTCCTCTAAAAAAA
```

FIGURE 6A

| | | | | | | | | | | | | | | | | | | | | | | | | |
|---|---|---|---|---|---|---|---|---|---|---|---|---|---|---|---|---|---|---|---|---|---|---|---|---|
| transduction | * | * | | * | | * | | * | * | | * | | | * | * | * | * | * | * | | * | | | * |
| pMD518_596 | G | D | . | V | . | G | . | P | . | D | G | . | V | . | G | . | D | E | S | . | I | T | G | . | E | . | A | . | S | . | . | G | . | . | . | . | L | V | . | A |
| Mcl | G | D | . | V | . | G | . | P | . | D | G | . | V | . | G | . | D | E | S | . | I | T | G | . | E | . | A | . | S | . | . | G | . | . | . | . | L | V | . | A |
| CopA | D | D | . | I | . | G | . | P | . | D | G | . | I | . | G | . | D | E | S | . | L | T | G | . | E | . | S | . | T | . | . | G | . | . | . | . | M | V | . | A |
| K+ ATPase (E. Faecalis) | G | D | . | V | . | G | . | P | . | D | G | . | I | . | G | . | D | E | S | . | V | T | G | . | E | . | S | . | S | . | . | G | . | . | . | . | L | V | . | A |
| Cd ATPase | G | D | . | V | . | G | . | A | . | D | G | . | I | . | Q | . | N | Q | A | . | I | T | G | . | E | . | S | . | T | . | . | G | . | . | . | . | L | V | . | A |
| H+/K+ ATPase | G | D | . | V | . | G | . | A | . | D | G | . | V | . | G | . | N | Q | T | . | I | T | G | . | E | . | S | . | T | . | . | G | . | . | . | . | L | M | . | A |
| FixI | G | D | . | V | . | G | . | P | . | D | G | . | V | . | G | . | D | R | S | . | V | N | G | . | E | . | S | . | S | . | . | G | . | . | . | . | M | V | . | A |
| K+ ATPase (E.Coli) | G | D | . | L | . | G | . | P | . | D | G | . | I | . | . | . | D | E | S | . | I | T | G | . | E | . | S | . | S | . | . | G | . | . | . | . | L | V | . | A |
| H+ ATPase | G | D | . | L | . | G | . | P | . | D | G | . | I | . | . | . | D | Q | S | . | I | T | G | . | E | . | S | . | S | . | . | G | . | . | . | . | L | V | . | A |
| ATPase S.c. | G | E | . | L | . | G | . | P | . | D | C | . | I | . | Q | . | D | Q | S | . | I | T | G | . | E | . | S | . | S | . | . | G | . | . | . | . | L | V | . | A |
| E1-E2 ATPase 1A | G | D | . | L | . | G | . | P | . | D | C | . | I | . | Q | . | D | E | A | . | L | T | G | . | E | . | S | . | S | . | . | G | . | . | . | . | L | L | . | V |

FIGURE 6B

| phospho_site | * | * | * | * | * | * | * * * | * | * | * * * |
|---|---|---|---|---|---|---|---|---|---|---|
| PWD621_723 | I.V | CPC.L | G | E | V | DKTGTII | G.P.V | V | E | SHPLG.AV... |
| Mc1 | I.V | CPC.L | G | E | V | DKTGTII | G.P.V | I | E | SHPLG.AI... |
| CopA | V.V | CPC.L | G | E | I | DKTGTII | G.P.V | I | E | SHPLG.AI... |
| K+ ATPase (E. Faecalis) | V.V | CPH.L | S | E | I | DKTGTLT | G.F.V | I | E | AHPLA.GI... |
| Cd ATPase | L.V | CPC.L | A | E | V | DKTGTLT | G.P.V | L | E | SHPLA.AI... |
| H+/K+ ATPase | L.V | CPC.L | A | E | I | DKTGTLT | G.P.V | L | E | SHPLA.AI... |
| FixI | V.V | CPC.L | A | E | V | DKTGTLT | G.P.L | L | A | SHPIA.AI... |
| K+ ATPase (E. Coli) | V.L | IPT.I | G | E | L | DKTGTII | G | | | |
| H+ ATPase 1 | L.I | VPV.L | G | E | L | DKTGTLT | N | | | |
| H+ ATPase 2 | L.I | VPV.L | G | E | L | DKTGTLT | N | | | |
| E1-E2 ATPase 1A | V.V | IPI.L | G | E | L | DKTGTLT | N | | | |

FIGURE 6C

| ATP | | | | | | | | | |
|---|---|---|---|---|---|---|---|---|---|
| | * | * | | * | * | | * | *** | ** |
| pWD836_956 | D.K | G. | GD | G.. | .P.K | V.M. | GDGVNDSP.L | .A.G.A...GTD....AD |
| Mc1 | D.K | G. | GD | G.. | .P.K | V.M. | GDGINDSP.L | .A.G.A...GTD....AD |
| CopA | D.K | G. | GD | G..A. | .P.K | V.M. | GDGINDAP.L | .A.G.A...GTD....AD |
| K+ ATPase (E. Faecalis) | D.K | N. | GD | G..A. | .P.K | V.M. | GDGINDAP.L | .A.G.A...GTD....AD |
| Cd ATPase | D.R | G. | GD | G..G. | .P.K | V.M. | GDGVNDAP.L | .S.G.A...GTD....AD |
| H+/K+ ATPase | D.R | G. | GD | G..S. | .P.K | V.M. | GDGVNDAP.L | .S.G.A...GTD....AD |
| FixI | D.R | G. | GD | G..A. | .P.K | A.V. | GDGINDAP.L | .A.S.A...AAD....AD |
| K+ ATPase (E. Coli) | D.K | G. | GD | G..A. | .P.K | V.M. | GDGINDAP.L | .A.A.A...GTQ....GN |
| E1-E2 ATPase | D.R | G. | GD | G..A. | .P.K | V.M. | GDGINDAP.L | .A.G.S...GSD....AG |
| H+ ATPase 1 | D.R | G. | GD | G..A. | .P.K | V.M. | GDGVNDAP.L | .A.G.A...ATD....AD |
| H+ ATPase 2 | D.R | G. | GD | G..A. | .P.K | V.F. | GDGINDAP.L | .A.G.A...ASD....AD |
| Mg++ ATPase | D.K | G. | GD | G..A. | .P.K | C.M. | GDGVNDAP.L | .A.G.S...AAD....SD |
| E1-E2 ATPase 1A | D.R | G. | GD | D..A. | .P.K | | GDGVNDAP.L | .A.G.A...ATD....AD |
| Ca++ ATPase | D.R | G. | GD | G..... | | V.V. | GDGTNDGP.L | .A.G.A...GTD....SD |

FIGURE 6D

| metal | | | | | | | | | |
|---|---|---|---|---|---|---|---|---|---|
| | * * | | | * | * * | | | * | |
| pWD1_60 | ..G | M T | C..C | ....E | .......G | V | ....V | .......I |
| Mc1(2) | ..G | M T | C..C | ....E | .......G | V | ....V | .......I |
| pWD115_174 | ..G | M H | C..C | ....E | .......G | V | ....V | .......V |
| Mc1(3) | ..G | M H | C..C | ....E | .......Y | V | ....V | .......V |
| pWD217_278 | ..G | M T | C..C | ....E | .......G | V | ....V | .......V |
| Mc1(4) | ..G | M T | C..C | ....E | .......G | V | ....V | .......V |
| pWD346_405 | ..G | M T | C..C | ....E | .......G | V | ....V | .......I |
| Mc1(5) | ..G | M T | C..C | ....E | .......G | I | ....V | .......V |
| pWD422_481 | ..G | M T | C..C | ....E | .......G | I | ....V | .......V |
| Mc1(6) | ..G | M T | C..C | ....E | .......G | I | ....V | .......I |
| CopA | ..G | M T | C..C | ....E | .......G | V | ....V | .......V |
| Cd ATPase | ..G | F S | C..C | ....E | .......G | V | ....V | .......V |
| Cd ATPase | ..G | F S | C..C | ....E | .......G | V | ....V | .......V |
| Hg++ reductase | ..G | M T | C..C | ....K | .......G | V | ....V | .......L |
| hyp protein 3 | ..G | M T | C..C | ....E | .......G | V | ....V | .......V |
| NR1 Hg++ resistance | ..G | M T | C..C | ....K | .......G | V | ....V | .......V |
| Hg++ transport | ..G | M T | C..C | ....K | .......G | V | ....V | .......V |
| Hg++ resistance | ..G | M T | C..C | ....K | .......G | V | ....V | .......L |

FIGURE 9

| | |
|---|---|
| pWD | CPC...P.......DKTG.......SE<u>H</u>PLGVA |
| Mc1 (Menkes) | CPC...P.......DKTG.......SE<u>H</u>PLGTA |
| CopA | CPC...P.......DKTG.......SE<u>H</u>PLGKA |
| fixI | CPC...P.......DKTG.......SR<u>H</u>PIAVA |
| CadA | CPC...P.......DKTG.......SQ<u>H</u>PLASA |

5,578,493

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:1:

GGATTACAGG YRTGAGCCA                                                         19

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:2:

RCCAYTGCAC TCCAGCCTG                                                         19

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:3:

CCCAGTGAGC AGCCTCTAAA                                                                   20

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:4:

AACAGAAATC AGGCCAGTGT G                                                              21

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:5:

CTGCCACCTA TTTTTGTAAA TAAAG                                                         25

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:6:

TGATCTGGTG GTTCAACTGG                                                                   20

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

(i i i) HYPOTHETICAL: NO (x i) SEQUENCE DESCRIPTION: SEQ ID NO:7:

ATCATACCTG GTTGTGCAAC C    21

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (x i) SEQUENCE DESCRIPTION: SEQ ID NO:8:

CCAGATGCTT CTTTCTAAAC ACACA    25

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (x i) SEQUENCE DESCRIPTION: SEQ ID NO:9:

CAAACTTTTA GTATGAGTCT ATCTCTCTCT    30

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (x i) SEQUENCE DESCRIPTION: SEQ ID NO:10:

TCATTAAAGT GAGGAGTGAG GTAAATG    27

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (x i) SEQUENCE DESCRIPTION: SEQ ID NO:11:

TTATGATGAA AAAAGTAATA TAAGAGGTCC C    31

(2) INFORMATION FOR SEQ ID NO:12:

(i) SEQUENCE CHARACTERISTICS:
        (A) LENGTH: 18 base pairs
        (B) TYPE: nucleic acid ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:12:

AGCTGTATCT GGGGTTGG  18

( 2 ) INFORMATION FOR SEQ ID NO:13:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:13:

AGTTTCTACA TGAATAAAAT CGTACTAGAA G  31

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:14:

GGTATCTTGT ATAATACTAC CTTCCATCA  29

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:15:

TTTAACTGGC ATGTTAATCT GGG  23

( 2 ) INFORMATION FOR SEQ ID NO:16:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:16:

CTCCCCCTCC TTGCCTGCAA CT  22

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:17:

CCTGGAACTG GAAGATGGCA 20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:18:

GGAGTTGGGG AGACCACAAT 20

( 2 ) INFORMATION FOR SEQ ID NO:19:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( x i ) SEQUENCE DESCRIPTION: SEQ ID NO:19:

AATAAA 6

( 2 ) INFORMATION FOR SEQ ID NO:20:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

Gly Xaa Xaa Cys Xaa Xaa Cys
1               5

( 2 ) INFORMATION FOR SEQ ID NO:21:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

Gly Asp Gly Xaa Asn Asp Xaa Pro Leu
1               5

(2) INFORMATION FOR SEQ ID NO:22:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (xi) SEQUENCE DESCRIPTION: SEQ ID NO:22:

CAGCTACCAG AGAAGGACAT GG             22

(2) INFORMATION FOR SEQ ID NO:23:

(i) SEQUENCE CHARACTERISTICS:
       (A) LENGTH: 8 amino acids
       (B) TYPE: amino acid
       (D) TOPOLOGY: linear (ii) MOLECULE TYPE: protein (xi) SEQUENCE DESCRIPTION: SEQ ID NO:23:

Ser Glu His Pro Leu Gly Val Ala
   1               5

(2) INFORMATION FOR SEQ ID NO:24:

(i) SEQUENCE CHARACTERISTICS:
       (A) LENGTH: 8 amino acids
       (B) TYPE: amino acid
       (D) TOPOLOGY: linear (ii) MOLECULE TYPE: protein (xi) SEQUENCE DESCRIPTION: SEQ ID NO:24:

Ser Glu His Pro Leu Gly Thr Ala
   1               5

(2) INFORMATION FOR SEQ ID NO:25:

(i) SEQUENCE CHARACTERISTICS:
       (A) LENGTH: 8 amino acids
       (B) TYPE: amino acid
       (D) TOPOLOGY: linear (ii) MOLECULE TYPE: protein (xi) SEQUENCE DESCRIPTION: SEQ ID NO:25:

Ser Glu His Pro Leu Gly Lys Ala
   1               5

(2) INFORMATION FOR SEQ ID NO:26:

(i) SEQUENCE CHARACTERISTICS:
       (A) LENGTH: 8 amino acids
       (B) TYPE: amino acid
       (D) TOPOLOGY: linear (ii) MOLECULE TYPE: protein (xi) SEQUENCE DESCRIPTION: SEQ ID NO:26:

Ser Arg His Pro Ile Ala Val Ala
   1               5

(2) INFORMATION FOR SEQ ID NO:27:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: protein ( x i ) SEQUENCE DESCRIPTION: SEQ ID NO:27:

Ser Gln His Pro Leu Ala Ser Ala
1               5

( 2 ) INFORMATION FOR SEQ ID NO:28:

( i ) SEQUENCE CHARACTERISTICS:
        ( A ) LENGTH: 5421 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo Sapiens ( i x ) FEATURE:
        ( A ) NAME/KEY: CDS
        ( B ) LOCATION: 1..3330

( x i ) SEQUENCE DESCRIPTION: SEQ ID NO:28:

```
GTG GAG GGC ATG ACC TGC CAG TCC TGT GTC AGC TCC ATT GAA GGC AAG      48
Val Glu Gly Met Thr Cys Gln Ser Cys Val Ser Ser Ile Glu Gly Lys
 1               5                  10                  15

GTC CGG AAA CTG CAA GGA GTA GTG AGA GTC AAA GTC TCA CTC AGC AAC      96
Val Arg Lys Leu Gln Gly Val Val Arg Val Lys Val Ser Leu Ser Asn
            20                  25                  30

CAA GAG GCC GTC ATC ACT TAT CAG CCT TAT CTC ATT CAG CCC GAA GAC     144
Gln Glu Ala Val Ile Thr Tyr Gln Pro Tyr Leu Ile Gln Pro Glu Asp
        35                  40                  45

CTC AGG GAC CAT GTA AAT GAC ATG GGA TTT GAA GCT GCC ATC AAG AGC     192
Leu Arg Asp His Val Asn Asp Met Gly Phe Glu Ala Ala Ile Lys Ser
    50                  55                  60

AAA GTG GCT CCC TTA AGC CTG GGA CCA ATT GAT ATT GAG CGG TTA CAA     240
Lys Val Ala Pro Leu Ser Leu Gly Pro Ile Asp Ile Glu Arg Leu Gln
65                  70                  75                  80

AGC ACT AAC CCA AAG AGA CCT TTA TCT TCT GCT AAC CAG AAT TTT AAT     288
Ser Thr Asn Pro Lys Arg Pro Leu Ser Ser Ala Asn Gln Asn Phe Asn
                85                  90                  95

AAT TCT GAG ACC TTG GGG CAC CAA GGA AGC CAT GTG GTC ACC CTC CAA     336
Asn Ser Glu Thr Leu Gly His Gln Gly Ser His Val Val Thr Leu Gln
            100                 105                 110

CTG AGA ATA GAT GGA ATG CAT TGT AAG TCT TGC GTC TTG AAT ATT GAA     384
Leu Arg Ile Asp Gly Met His Cys Lys Ser Cys Val Leu Asn Ile Glu
        115                 120                 125

GAA AAT ATT GGC CAG CTC CTA GGG GTT CAA AGT ATT CAA GTG TCC TTG     432
Glu Asn Ile Gly Gln Leu Leu Gly Val Gln Ser Ile Gln Val Ser Leu
    130                 135                 140

GAG AAC AAA ACT GCC CAA GTA AAG TAT GAC CCT TCT TGT ACC AGC CCA     480
Glu Asn Lys Thr Ala Gln Val Lys Tyr Asp Pro Ser Cys Thr Ser Pro
145                 150                 155                 160

GTG GCT CTG CAG AGG GCT ATC GAG GCA CTT CCA CCT GGG AAT TTT AAA     528
Val Ala Leu Gln Arg Ala Ile Glu Ala Leu Pro Pro Gly Asn Phe Lys
                165                 170                 175

GTT TCT CTT CCT GAT GGA GCC GAA GGG AGT GGG ACA GAT CAC AGG TCT     576
Val Ser Leu Pro Asp Gly Ala Glu Gly Ser Gly Thr Asp His Arg Ser
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 180 |     |     |     |     | 185 |     |     |     |     | 190 |     |     |      |
| TCC | AGT | TCT | CAT | TCC | CCT | GGC | TCC | CCA | CCG | AGA | AAC | CAG | GTC | CAG | GGC | 624  |
| Ser | Ser | Ser | His | Ser | Pro | Gly | Ser | Pro | Pro | Arg | Asn | Gln | Val | Gln | Gly |      |
|     |     | 195 |     |     |     |     | 200 |     |     |     |     | 205 |     |     |     |      |
| ACA | TGC | AGT | ACC | ACT | CTG | ATT | GCC | ATT | GCC | GGC | ATG | ACC | TGT | GCA | TCC | 672  |
| Thr | Cys | Ser | Thr | Thr | Leu | Ile | Ala | Ile | Ala | Gly | Met | Thr | Cys | Ala | Ser |      |
|     | 210 |     |     |     |     | 215 |     |     |     |     | 220 |     |     |     |     |      |
| TGT | GTC | CAT | TCC | ATT | GAA | GGC | ATG | ATC | TCC | CAA | CTG | GAA | GGG | GTG | CAG | 720  |
| Cys | Val | His | Ser | Ile | Glu | Gly | Met | Ile | Ser | Gln | Leu | Glu | Gly | Val | Gln |      |
| 225 |     |     |     |     | 230 |     |     |     |     | 235 |     |     |     |     | 240 |      |
| CAA | ATA | TCG | GTG | TCT | TTG | GCC | GAA | GGG | ACT | GCA | ACA | GTT | CTT | TAT | AAT | 768  |
| Gln | Ile | Ser | Val | Ser | Leu | Ala | Glu | Gly | Thr | Ala | Thr | Val | Leu | Tyr | Asn |      |
|     |     |     |     | 245 |     |     |     |     | 250 |     |     |     |     | 255 |     |      |
| CCC | TCT | GTA | ATT | AGC | CCA | GAA | GAA | CTC | AGA | GCT | GCT | ATA | GAA | GAC | ATG | 816  |
| Pro | Ser | Val | Ile | Ser | Pro | Glu | Glu | Leu | Arg | Ala | Ala | Ile | Glu | Asp | Met |      |
|     |     |     | 260 |     |     |     |     | 265 |     |     |     |     | 270 |     |     |      |
| GGA | TTT | GAG | GCT | TCA | GTC | GTT | TCT | GAA | AGC | TGT | TCT | ACT | AAC | CCT | CTT | 864  |
| Gly | Phe | Glu | Ala | Ser | Val | Val | Ser | Glu | Ser | Cys | Ser | Thr | Asn | Pro | Leu |      |
|     |     | 275 |     |     |     |     | 280 |     |     |     |     | 285 |     |     |     |      |
| GGA | AAC | CAC | AGT | GCT | GGG | AAT | TCC | ATG | GTG | CAA | ACT | ACA | GAT | GGT | ACA | 912  |
| Gly | Asn | His | Ser | Ala | Gly | Asn | Ser | Met | Val | Gln | Thr | Thr | Asp | Gly | Thr |      |
|     | 290 |     |     |     |     | 295 |     |     |     |     | 300 |     |     |     |     |      |
| CCT | ACA | TCT | GTG | CAG | GAA | GTG | GCT | CCC | CAC | ACT | GGG | AGG | CTC | CCT | GCA | 960  |
| Pro | Thr | Ser | Val | Gln | Glu | Val | Ala | Pro | His | Thr | Gly | Arg | Leu | Pro | Ala |      |
| 305 |     |     |     |     | 310 |     |     |     |     | 315 |     |     |     |     | 320 |      |
| AAC | CAT | GCC | CCG | GAC | ATC | TTG | GCA | AAG | TCC | CCA | CAA | TCA | ACC | AGA | GCA | 1008 |
| Asn | His | Ala | Pro | Asp | Ile | Leu | Ala | Lys | Ser | Pro | Gln | Ser | Thr | Arg | Ala |      |
|     |     |     |     | 325 |     |     |     |     | 330 |     |     |     |     | 335 |     |      |
| GTG | GCA | CCG | CAG | AAG | TGC | TTC | TTA | CAG | ATC | AAA | GGC | ATG | ACC | TGT | GCA | 1056 |
| Val | Ala | Pro | Gln | Lys | Cys | Phe | Leu | Gln | Ile | Lys | Gly | Met | Thr | Cys | Ala |      |
|     |     |     | 340 |     |     |     |     | 345 |     |     |     |     | 350 |     |     |      |
| TCC | TGT | GTG | TCT | AAC | ATA | GAA | AGG | AAT | CTG | CAG | AAA | GAA | GCT | GGT | GTT | 1104 |
| Ser | Cys | Val | Ser | Asn | Ile | Glu | Arg | Asn | Leu | Gln | Lys | Glu | Ala | Gly | Val |      |
|     |     | 355 |     |     |     |     | 360 |     |     |     |     | 365 |     |     |     |      |
| CTC | TCC | GTG | TTG | GTT | GCC | TTG | ATG | GCA | GGA | AAG | GCA | GAG | ATC | AAG | TAT | 1152 |
| Leu | Ser | Val | Leu | Val | Ala | Leu | Met | Ala | Gly | Lys | Ala | Glu | Ile | Lys | Tyr |      |
|     | 370 |     |     |     |     | 375 |     |     |     |     | 380 |     |     |     |     |      |
| GAC | CCA | GAG | GTC | ATC | CAG | CCC | CTC | GAG | ATA | GCT | CAG | TTC | ATC | CAG | GAC | 1200 |
| Asp | Pro | Glu | Val | Ile | Gln | Pro | Leu | Glu | Ile | Ala | Gln | Phe | Ile | Gln | Asp |      |
| 385 |     |     |     |     | 390 |     |     |     |     | 395 |     |     |     |     | 400 |      |
| CTG | GGT | TTT | GAG | GCA | GCA | GTC | ATG | GAG | GAC | TAC | GCA | GGC | TCC | GAT | GGC | 1248 |
| Leu | Gly | Phe | Glu | Ala | Ala | Val | Met | Glu | Asp | Tyr | Ala | Gly | Ser | Asp | Gly |      |
|     |     |     |     | 405 |     |     |     |     | 410 |     |     |     |     | 415 |     |      |
| AAC | ATT | GAG | CTG | ACA | ATC | ACA | GGG | ATG | ACC | TGC | GCG | TCC | TGT | GTC | CAC | 1296 |
| Asn | Ile | Glu | Leu | Thr | Ile | Thr | Gly | Met | Thr | Cys | Ala | Ser | Cys | Val | His |      |
|     |     |     | 420 |     |     |     |     | 425 |     |     |     |     | 430 |     |     |      |
| AAC | ATA | GAG | TCC | AAA | CTC | ACG | AGG | ACA | AAT | GGC | ATC | ACT | TAT | GCC | TCC | 1344 |
| Asn | Ile | Glu | Ser | Lys | Leu | Thr | Arg | Thr | Asn | Gly | Ile | Thr | Tyr | Ala | Ser |      |
|     |     | 435 |     |     |     |     | 440 |     |     |     |     | 445 |     |     |     |      |
| GTT | GCC | CTT | GCC | ACC | AGC | AAA | GCC | CTT | GTT | AAG | TTT | GAC | CCG | GAA | ATT | 1392 |
| Val | Ala | Leu | Ala | Thr | Ser | Lys | Ala | Leu | Val | Lys | Phe | Asp | Pro | Glu | Ile |      |
|     | 450 |     |     |     |     | 455 |     |     |     |     | 460 |     |     |     |     |      |
| ATC | GGT | CCA | CGG | GAT | ATT | ATC | AAA | ATT | ATT | GAG | AGC | AAA | ACC | TCA | GAA | 1440 |
| Ile | Gly | Pro | Arg | Asp | Ile | Ile | Lys | Ile | Ile | Glu | Ser | Lys | Thr | Ser | Glu |      |
| 465 |     |     |     |     | 470 |     |     |     |     | 475 |     |     |     |     | 480 |      |
| GCC | CTG | GCT | AAA | CTC | ATG | TCT | CTC | CAA | GCC | ACA | GAA | GCC | ACC | GTT | GTG | 1488 |
| Ala | Leu | Ala | Lys | Leu | Met | Ser | Leu | Gln | Ala | Thr | Glu | Ala | Thr | Val | Val |      |
|     |     |     |     | 485 |     |     |     |     | 490 |     |     |     |     | 495 |     |      |
| ACC | CTT | GGT | GAG | GAC | AAT | TTA | ATC | ATC | AGG | GAG | GAG | CAA | GTC | CCC | ATG | 1536 |
| Thr | Leu | Gly | Glu | Asp | Asn | Leu | Ile | Ile | Arg | Glu | Glu | Gln | Val | Pro | Met |      |

-continued

|  |  |  |  | 500 |  |  |  |  | 505 |  |  |  |  | 510 |  |  |  |
|---|---|---|---|---|---|---|---|---|---|---|---|---|---|---|---|---|---|
| GAG | CTG | GTG | CAG | CGG | GGC | GAT | ATC | GTC | AAG | GTG | GTC | CCT | GGG | GGA | AAG | | 1584 |
| Glu | Leu | Val 515 | Gln | Arg | Gly | Asp | Ile 520 | Val | Lys | Val | Val | Pro 525 | Gly | Gly | Lys | | |
| TTT | CCA | GTG | GAT | GGG | AAA | GTC | CTG | GAA | GGC | AAT | ACC | ATG | GCT | GAT | GAG | | 1632 |
| Phe | Pro 530 | Val | Asp | Gly | Lys | Val 535 | Leu | Glu | Gly | Asn | Thr | Met 540 | Ala | Asp | Glu | | |
| TCC | CTC | ATC | ACA | GGA | GAA | GCC | ATG | CCA | GTC | ACT | AAG | AAA | CCC | GGA | AGC | | 1680 |
| Ser 545 | Leu | Ile | Thr | Gly | Glu 550 | Ala | Met | Pro | Val | Thr 555 | Lys | Lys | Pro | Gly | Ser 560 | | |
| ACT | GTA | ATT | GCG | AGG | TCT | ATA | AAT | GCA | CAT | GGC | TCT | GTG | CTC | ATT | AAA | | 1728 |
| Thr | Val | Ile | Ala | Arg 565 | Ser | Ile | Asn | Ala | His 570 | Gly | Ser | Val | Leu | Ile 575 | Lys | | |
| GCT | ACC | CAC | GTG | GGC | AAT | GAC | ACC | ACT | TTG | GCT | CAG | ATT | GTG | AAA | CTG | | 1776 |
| Ala | Thr | His | Val 580 | Gly | Asn | Asp | Thr | Thr 585 | Leu | Ala | Gln | Ile | Val 590 | Lys | Leu | | |
| GTG | GAA | GAG | GCT | CAG | ATG | TCA | AAG | AAC | CCC | AAC | AAG | CAC | ATC | TCC | CAG | | 1824 |
| Val | Glu | Glu 595 | Ala | Gln | Met | Ser | Lys 600 | Asn | Pro | Asn | Lys | His 605 | Ile | Ser | Gln | | |
| ACA | GAG | GTG | ATC | ATC | CGG | TTT | GCT | TTC | CAG | ACG | TCC | ATC | ACG | GTG | CTG | | 1872 |
| Thr | Glu 610 | Val | Ile | Ile | Arg | Phe 615 | Ala | Phe | Gln | Thr | Ser 620 | Ile | Thr | Val | Leu | | |
| TGC | ATT | GCC | TGC | CCC | TGC | TCC | CTG | GGG | CTG | GCC | ACG | CCC | ACG | GCT | GTC | | 1920 |
| Cys 625 | Ile | Ala | Cys | Pro | Cys 630 | Ser | Leu | Gly | Leu | Ala 635 | Thr | Pro | Thr | Ala | Val 640 | | |
| ATG | GTG | GGC | ACC | GGG | GTG | GCC | GCG | CAG | AAC | GGC | ATC | CTC | ATC | AAG | GGA | | 1968 |
| Met | Val | Gly | Thr | Gly 645 | Val | Ala | Ala | Gln | Asn 650 | Gly | Ile | Leu | Ile | Lys 655 | Gly | | |
| GGC | AAG | CCC | CTG | GAG | ATG | GCG | CAC | AAG | ATA | AAG | ACT | GTG | ATG | TTT | GAC | | 2016 |
| Gly | Lys | Pro | Leu 660 | Glu | Met | Ala | His | Lys 665 | Ile | Lys | Thr | Val | Met 670 | Phe | Asp | | |
| AAG | ACT | GGC | ACC | ATT | ACC | CAT | GGC | GTC | CCC | AGG | GTC | ATG | CGG | GTG | CTC | | 2064 |
| Lys | Thr | Gly 675 | Thr | Ile | Thr | His | Gly 680 | Val | Pro | Arg | Val | Met 685 | Arg | Val | Leu | | |
| CTG | CTG | GGG | GAT | GTG | GCC | ACA | CTG | CCC | CTC | AGG | AAG | GTT | CTG | GCT | GTG | | 2112 |
| Leu | Leu | Gly 690 | Asp | Val | Ala | Thr | Leu 695 | Pro | Leu | Arg | Lys | Val 700 | Leu | Ala | Val | | |
| GTG | GGG | ACT | GCG | GAG | GCC | AGC | AGT | GAA | CAC | CCC | TTG | GGC | GTG | GCA | GTC | | 2160 |
| Val 705 | Gly | Thr | Ala | Glu | Ala 710 | Ser | Ser | Glu | His | Pro 715 | Leu | Gly | Val | Ala | Val 720 | | |
| ACC | AAA | TAC | TGT | AAA | GAG | GAA | CTT | GGA | ACA | GAG | ACC | TTG | GGA | TAC | TGC | | 2208 |
| Thr | Lys | Tyr | Cys | Lys 725 | Glu | Glu | Leu | Gly | Thr 730 | Glu | Thr | Leu | Gly | Tyr 735 | Cys | | |
| ACG | GAC | TTC | CAG | GCA | GTG | CCA | GGC | TGT | GGA | ATT | GGG | TGC | AAA | GTC | AGC | | 2256 |
| Thr | Asp | Phe | Gln 740 | Ala | Val | Pro | Gly | Cys 745 | Gly | Ile | Gly | Cys | Lys 750 | Val | Ser | | |
| AAC | GTG | GAA | GGC | ATC | CTG | GCC | CAC | AGT | GAG | CGC | CCT | TTG | AGT | GCA | CCG | | 2304 |
| Asn | Val | Glu 755 | Gly | Ile | Leu | Ala | His 760 | Ser | Glu | Arg | Pro | Leu 765 | Ser | Ala | Pro | | |
| GCC | AGT | CAC | CTG | AAT | GAG | GCT | GGC | AGC | CTT | CCC | GCA | GAA | AAA | GAT | GCA | | 2352 |
| Ala | Ser | His 770 | Leu | Asn | Glu | Ala | Gly 775 | Ser | Leu | Pro | Ala | Glu 780 | Lys | Asp | Ala | | |
| GTC | CCC | CAG | ACC | TTC | TCT | GTG | CTG | ATT | GGA | AAC | CGT | GAG | TGG | CTG | AGG | | 2400 |
| Val 785 | Pro | Gln | Thr | Phe | Ser 790 | Val | Leu | Ile | Gly | Asn 795 | Arg | Glu | Trp | Leu | Arg 800 | | |
| CGC | AAC | GGT | TTA | ACC | ATT | TCT | AGC | GAT | GTC | AGC | GAC | GCT | ATG | ACA | GAC | | 2448 |
| Arg | Asn | Gly | Leu | Thr 805 | Ile | Ser | Ser | Asp | Val 810 | Ser | Asp | Ala | Met | Thr 815 | Asp | | |
| CAC | GAG | ATG | AAA | GGA | CAG | ACA | GCC | ATC | CTG | GTG | GCT | ATT | GAC | GGT | GTG | | 2496 |
| His | Glu | Met | Lys | Gly | Gln | Thr | Ala | Ile | Leu | Val | Ala | Ile | Asp | Gly | Val | | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 820 |     |     |     |     |     | 825 |     |     |     |     | 830 |      |
| CTC | TGT | GGG | ATG | ATC | GCA | ATC | GCA | GAC | GCT | GTC | AAG | CAG | GAG | GCT | GCC | 2544 |
| Leu | Cys | Gly | Met | Ile | Ala | Ile | Ala | Asp | Ala | Val | Lys | Gln | Glu | Ala | Ala |      |
|     |     | 835 |     |     |     |     | 840 |     |     |     |     | 845 |     |     |     |      |
| CTG | GCT | GTG | CAC | ACG | CTG | CAG | AGC | ATG | GGT | GTG | GAC | GTG | GTT | CTG | ATC | 2592 |
| Leu | Ala | Val | His | Thr | Leu | Gln | Ser | Met | Gly | Val | Asp | Val | Val | Leu | Ile |      |
|     | 850 |     |     |     |     | 855 |     |     |     |     | 860 |     |     |     |     |      |
| ACG | GGG | GAC | AAC | CGG | AAG | ACA | GCC | AGA | GCT | ATT | GCC | ACC | CAG | GTT | GGC | 2640 |
| Thr | Gly | Asp | Asn | Arg | Lys | Thr | Ala | Arg | Ala | Ile | Ala | Thr | Gln | Val | Gly |      |
| 865 |     |     |     |     | 870 |     |     |     |     | 875 |     |     |     |     | 880 |      |
| ATC | AAC | AAA | GTC | TTT | GCA | GAG | GTG | CTG | CCT | TCG | CAC | AAG | GTG | GCC | AAG | 2688 |
| Ile | Asn | Lys | Val | Phe | Ala | Glu | Val | Leu | Pro | Ser | His | Lys | Val | Ala | Lys |      |
|     |     |     |     | 885 |     |     |     |     | 890 |     |     |     |     | 895 |     |      |
| GTC | CAG | GAG | CTC | CAG | AAT | AAA | GGG | AAG | AAA | GTC | GCC | ATG | GTG | GGG | GAT | 2736 |
| Val | Gln | Glu | Leu | Gln | Asn | Lys | Gly | Lys | Lys | Val | Ala | Met | Val | Gly | Asp |      |
|     |     |     | 900 |     |     |     |     | 905 |     |     |     |     | 910 |     |     |      |
| GGG | GTC | AAT | GAC | TCC | CCG | GCC | TTG | GCC | CAG | GCA | GAC | ATG | GGT | GTG | GCC | 2784 |
| Gly | Val | Asn | Asp | Ser | Pro | Ala | Leu | Ala | Gln | Ala | Asp | Met | Gly | Val | Ala |      |
|     |     | 915 |     |     |     |     | 920 |     |     |     |     | 925 |     |     |     |      |
| ATT | GGC | ACC | GGC | ACG | GAT | GTG | GCC | ATC | GAG | GCA | GCC | GAC | GTC | GTC | CTT | 2832 |
| Ile | Gly | Thr | Gly | Thr | Asp | Val | Ala | Ile | Glu | Ala | Ala | Asp | Val | Val | Leu |      |
| 930 |     |     |     |     | 935 |     |     |     |     | 940 |     |     |     |     |     |      |
| ATC | AGA | AAT | GAT | TTG | CTG | GAT | GTG | GTG | GCT | AGC | ATT | CAC | CTT | TCC | AAG | 2880 |
| Ile | Arg | Asn | Asp | Leu | Leu | Asp | Val | Val | Ala | Ser | Ile | His | Leu | Ser | Lys |      |
| 945 |     |     |     |     | 950 |     |     |     |     | 955 |     |     |     |     | 960 |      |
| AGG | ACT | GTC | CGA | AGG | ATA | CGC | ATC | AAC | CTG | GTC | CTG | GCA | CTG | ATT | TAT | 2928 |
| Arg | Thr | Val | Arg | Arg | Ile | Arg | Ile | Asn | Leu | Val | Leu | Ala | Leu | Ile | Tyr |      |
|     |     |     |     | 965 |     |     |     |     | 970 |     |     |     |     | 975 |     |      |
| AAC | CTG | GTT | GGG | ATA | CCC | ATT | GCA | GCA | GGT | GTC | TTC | ATG | CCC | ATC | GGC | 2976 |
| Asn | Leu | Val | Gly | Ile | Pro | Ile | Ala | Ala | Gly | Val | Phe | Met | Pro | Ile | Gly |      |
|     |     |     | 980 |     |     |     |     | 985 |     |     |     |     | 990 |     |     |      |
| ATT | GTG | CTG | CAG | CCC | TGG | ATG | GGC | TCA | GCG | GCC | ATG | GCA | GCC | TCC | TCT | 3024 |
| Ile | Val | Leu | Gln | Pro | Trp | Met | Gly | Ser | Ala | Ala | Met | Ala | Ala | Ser | Ser |      |
|     |     | 995 |     |     |     |     | 1000|     |     |     |     | 1005|     |     |     |      |
| GTG | TCT | GTG | GTG | CTC | TCA | TCC | CTG | CAG | CTC | AAG | TGC | TAT | AAG | AAG | CCT | 3072 |
| Val | Ser | Val | Val | Leu | Ser | Ser | Leu | Gln | Leu | Lys | Cys | Tyr | Lys | Lys | Pro |      |
|     |     | 1010|     |     |     |     | 1015|     |     |     |     | 1020|     |     |     |      |
| GAC | CTG | GAG | AGG | TAT | GAG | GCA | CAG | GCG | CAT | GGC | CAC | ATG | AAG | CCC | CTG | 3120 |
| Asp | Leu | Glu | Arg | Tyr | Glu | Ala | Gln | Ala | His | Gly | His | Met | Lys | Pro | Leu |      |
| 1025|     |     |     |     | 1030|     |     |     |     | 1035|     |     |     |     | 1040|      |
| ACG | GCA | TCC | CAG | GTC | AGT | GTG | CAC | ATA | GGC | ATG | GAT | GAC | AGG | TGG | CGG | 3168 |
| Thr | Ala | Ser | Gln | Val | Ser | Val | His | Ile | Gly | Met | Asp | Asp | Arg | Trp | Arg |      |
|     |     |     |     | 1045|     |     |     |     | 1050|     |     |     |     | 1055|     |      |
| GAC | TCC | CCC | AGG | GCC | ACA | CCA | TGG | GAC | CAG | GTC | AGC | TAT | GTC | AGC | CAG | 3216 |
| Asp | Ser | Pro | Arg | Ala | Thr | Pro | Trp | Asp | Gln | Val | Ser | Tyr | Val | Ser | Gln |      |
|     |     |     | 1060|     |     |     |     | 1065|     |     |     |     | 1070|     |     |      |
| GTG | TCG | CTG | TCC | TCC | CTG | ACG | TCC | GAC | AAG | CCA | TCT | CGG | CAC | AGC | GCT | 3264 |
| Val | Ser | Leu | Ser | Ser | Leu | Thr | Ser | Asp | Lys | Pro | Ser | Arg | His | Ser | Ala |      |
|     |     | 1075|     |     |     |     | 1080|     |     |     |     | 1085|     |     |     |      |
| GCA | GCA | GAC | GAT | GAT | GGG | GAC | AAG | TGG | TCT | CTG | CTC | CTG | AAT | GGC | AGG | 3312 |
| Ala | Ala | Asp | Asp | Asp | Gly | Asp | Lys | Trp | Ser | Leu | Leu | Leu | Asn | Gly | Arg |      |
|     |     | 1090|     |     |     |     | 1095|     |     |     |     | 1100|     |     |     |      |
| GAT | GAG | GAG | CAG | TAC | ATC | TGATGACTTC | AGGCAGGCGG | GCCGGGGCAG |     |     |     |     |     |     | 3360 |
| Asp | Glu | Glu | Gln | Tyr | Ile |     |     |     |     |     |     |     |     |     |     |      |
| 1105|     |     |     |     | 1110|     |     |     |     |     |     |     |     |     |     |      |

| | | | | |
|---|---|---|---|---|
| GGACTTGCCT | CCACTCACCA | CAAGCTGAGC | AGGACAGCCA | GCAGCAGGAT | GGGCTGAGCT | 3420 |
| AGCCTCCAGC | TTTGGGGACT | TCCGCTCCCT | GGATATGTCC | AGTCATCCTG | CCCTGCAGCA | 3480 |
| CGCGGCCTTG | TCTGGGTGCA | GCTGGGCTTG | GCCTGGAGAG | GACGGCCCTG | CCTGCCTCTT | 3540 |

| | | | | | |
|---|---|---|---|---|---|
| GGCCTCACGG | GACCGTCAGC | ATGGGCTTTG | TCTTGGACTC | TAGTCCTTGG | CTGGACTGTA | 3600 |
| GAAGGTGAGA | GGCGAGTCAC | CCTCCTCACA | GACCTCTGCT | GGAGTATTT | AGGATGACTG | 3660 |
| CTGTGAAATG | GAGAACAGTT | TCATCAGGAC | CAAAAAACCT | CACTGGGCCT | TTCCAGAGAA | 3720 |
| CTGCAGACCT | CACTGTCAGG | GTCTTTCTGA | TGACGCCTGT | CTGTGTGCAT | CATGTTTCTG | 3780 |
| AGACCACAGT | TTACCTCAGG | TGTGCCTGTT | GCTTCTTCC | TGCATAGTCT | GTTCCTTTCT | 3840 |
| TCGTACATAG | TCTGTTCCTT | TTCTCTCCTG | TGTGCTTGTC | AGTGGGGACC | CCTCGCAACC | 3900 |
| CTGCCTGTCA | CCTGGGAGGG | TGGGACCAAT | GTCCTTGTGG | TCTTTGCTGC | TGCTCTCAGG | 3960 |
| CGCTTCTCCA | ATGCTCTGGA | GTGTGCATTT | CAGCTTGAAC | CTGCTTCCTG | GCTCACACAT | 4020 |
| CCCCAGCCAG | GGAGCTTGCC | ACACTCTTCT | TCAAGTTGAG | GAGAGTTCTT | TTTTGCTTAA | 4080 |
| AGCCCCCTTC | TCCATGGAGT | GTTGGCTTCT | CAATAGAGTG | TTGTTGCTGA | CCAGCTGGAG | 4140 |
| TGAGGGCCTC | AGAGCCTGAC | CTGAGAGTCC | GTACTCGGCT | TCCTGTGGGG | TGTAGGTTCT | 4200 |
| CGCGATTCAG | GACGTCCTTC | CATATCCCTG | CCCAGCCTGT | GGTGCTTGAA | ACGTTTGCCC | 4260 |
| CATGGGAAAC | GTATGTGTGC | AGGAGCCTCC | CTGCACGGCC | CAAGGGGCTT | CGTTTTCAGT | 4320 |
| CTTCTGACTG | TCACCTCGTG | GGGTTCAGTA | GAGAATTCAA | TTACTAGCGC | CTGGCCTTGT | 4380 |
| GTGGCTTGGA | GGAAATGGTA | CTGCCCAAAT | AGGAGGAAAA | CACAGCCTCC | CTGAGCCTGC | 4440 |
| ATTCTGCACG | CTGCCCAGGG | GCTTCAGAAA | GGAGTGGCC | ACAGCACCCC | GAAGGGAGCA | 4500 |
| TCTATTTACC | TGGCAGTGGC | TCTCAGAGCA | GCAGAACGGG | TTCAGTTTTA | GACTCTGAAG | 4560 |
| TTGGTTGTGA | TTGACAGAAC | CCTTTGGGAG | CAAACTAGTA | GAGTTGGATT | AAATTCTGGG | 4620 |
| TGAAACCCTT | TTCTCCCACA | CAAAATAGTT | TTAGTGATTT | TTTTCATTGT | CCATTACTTG | 4680 |
| CCAGGGGCAG | TTTTAGCAGC | ACTTTTGATA | GATTACGTCT | AATCCTCCCA | ACCAACCAGC | 4740 |
| AGGGTAGCTA | TTACTGTCCA | CATTTTACAG | GCAAGGAAAC | AGGCTCCAAG | AGGCTGAGGA | 4800 |
| CTTTGCCCAG | GATGACATAG | CCAATGGACA | AGCAGTGTCT | GTCAGCTGTG | AAGGCTTCAC | 4860 |
| TCTTATTGTC | CTTCTACCTT | GAATAGAAGT | TTTCCTGATA | AGAATAAACG | AGGAAAAGGT | 4920 |
| CCTTGCCTCC | TGGAAGAACA | AATCTACCAG | GTGATCTATT | CATTGTTTCA | ACTCAGAATG | 4980 |
| CACTTGATTC | AGGAGGTCAT | CTGACCTTCA | CCTTGGATGG | TTAGTTTCAC | TTTTTACATA | 5040 |
| TAGTTTTTGC | AGGGTTTTAT | TTTATAAAAT | CCAAGCGCGC | TGTTGATTGT | GTTTTCCTTG | 5100 |
| TTTTCAGCCC | CCCGACTCCA | GCCCGCAGCA | CATTTCCGCT | GTCCGTCAGT | AATTGTGTCC | 5160 |
| TCTCTTTATG | CTTGCTTGGG | GAATGTTGTT | TTCTGACTAG | GCTGATCATT | ATCTAAAGAA | 5220 |
| TCTAATTCTG | TTGATTTTTA | AAACTTTTAG | GACCATAAAC | GTTGTGTTCA | TATATGGACA | 5280 |
| TGGAAATATT | TATATAATTT | TATAGAAAAT | AACCTTTTAG | ATGGTCAAAG | TGTAAGGAGT | 5340 |
| TTTTTTGTCA | GATAATCATT | TCTACTTCAA | AAACATTTCA | TGCAATATTA | GAATAAAGTT | 5400 |
| CCTGTCATTC | CTCTAAAAAA | A | | | | 5421 |

( 2 ) INFORMATION FOR SEQ ID NO:29:

( i ) SEQUENCE CHARACTERISTICS:
        ( A ) LENGTH: 1110 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

| Val | Glu | Gly | Met | Thr | Cys | Gln | Ser | Cys | Val | Ser | Ser | Ile | Glu | Gly | Lys |
|---|---|---|---|---|---|---|---|---|---|---|---|---|---|---|---|
| 1 | | | | 5 | | | | | 10 | | | | | 15 | |

| Val | Arg | Lys | Leu | Gln | Gly | Val | Val | Arg | Val | Lys | Val | Ser | Leu | Ser | Asn |

-continued

```
                20                           25                          30
Gln  Glu  Ala  Val  Ile  Thr  Tyr  Gln  Pro  Tyr  Leu  Ile  Gln  Pro  Glu  Asp
          35                      40                 45

Leu  Arg  Asp  His  Val  Asn  Asp  Met  Gly  Phe  Glu  Ala  Ala  Ile  Lys  Ser
 50                       55                               60

Lys  Val  Ala  Pro  Leu  Ser  Leu  Gly  Pro  Ile  Asp  Ile  Glu  Arg  Leu  Gln
 65                  70                       75                            80

Ser  Thr  Asn  Pro  Lys  Arg  Pro  Leu  Ser  Ser  Ala  Asn  Gln  Asn  Phe  Asn
                    85                        90                      95

Asn  Ser  Glu  Thr  Leu  Gly  His  Gln  Gly  Ser  His  Val  Val  Thr  Leu  Gln
               100                  105                      110

Leu  Arg  Ile  Asp  Gly  Met  His  Cys  Lys  Ser  Cys  Val  Leu  Asn  Ile  Glu
               115                 120                       125

Glu  Asn  Ile  Gly  Gln  Leu  Leu  Gly  Val  Gln  Ser  Ile  Gln  Val  Ser  Leu
     130                      135                      140

Glu  Asn  Lys  Thr  Ala  Gln  Val  Lys  Tyr  Asp  Pro  Ser  Cys  Thr  Ser  Pro
145                      150                      155                      160

Val  Ala  Leu  Gln  Arg  Ala  Ile  Glu  Ala  Leu  Pro  Pro  Gly  Asn  Phe  Lys
                    165                      170                      175

Val  Ser  Leu  Pro  Asp  Gly  Ala  Glu  Gly  Ser  Gly  Thr  Asp  His  Arg  Ser
               180                      185                      190

Ser  Ser  Ser  His  Ser  Pro  Gly  Ser  Pro  Pro  Arg  Asn  Gln  Val  Gln  Gly
          195                      200                      205

Thr  Cys  Ser  Thr  Thr  Leu  Ile  Ala  Ile  Ala  Gly  Met  Thr  Cys  Ala  Ser
     210                      215                      220

Cys  Val  His  Ser  Ile  Glu  Gly  Met  Ile  Ser  Gln  Leu  Glu  Gly  Val  Gln
225                      230                      235                      240

Gln  Ile  Ser  Val  Ser  Leu  Ala  Glu  Gly  Thr  Ala  Thr  Val  Leu  Tyr  Asn
                    245                      250                      255

Pro  Ser  Val  Ile  Ser  Pro  Glu  Glu  Leu  Arg  Ala  Ala  Ile  Glu  Asp  Met
               260                      265                      270

Gly  Phe  Glu  Ala  Ser  Val  Val  Ser  Glu  Ser  Cys  Ser  Thr  Asn  Pro  Leu
          275                      280                      285

Gly  Asn  His  Ser  Ala  Gly  Asn  Ser  Met  Val  Gln  Thr  Thr  Asp  Gly  Thr
     290                      295                      300

Pro  Thr  Ser  Val  Gln  Glu  Val  Ala  Pro  His  Thr  Gly  Arg  Leu  Pro  Ala
305                      310                      315                      320

Asn  His  Ala  Pro  Asp  Ile  Leu  Ala  Lys  Ser  Pro  Gln  Ser  Thr  Arg  Ala
                    325                      330                      335

Val  Ala  Pro  Gln  Lys  Cys  Phe  Leu  Gln  Ile  Lys  Gly  Met  Thr  Cys  Ala
               340                      345                      350

Ser  Cys  Val  Ser  Asn  Ile  Glu  Arg  Asn  Leu  Gln  Lys  Glu  Ala  Gly  Val
          355                      360                      365

Leu  Ser  Val  Leu  Val  Ala  Leu  Met  Ala  Gly  Lys  Ala  Glu  Ile  Lys  Tyr
     370                      375                      380

Asp  Pro  Glu  Val  Ile  Gln  Pro  Leu  Glu  Ile  Ala  Gln  Phe  Ile  Gln  Asp
385                      390                      395                      400

Leu  Gly  Phe  Glu  Ala  Ala  Val  Met  Glu  Asp  Tyr  Ala  Gly  Ser  Asp  Gly
                    405                      410                      415

Asn  Ile  Glu  Leu  Thr  Ile  Thr  Gly  Met  Thr  Cys  Ala  Ser  Cys  Val  His
               420                      425                      430

Asn  Ile  Glu  Ser  Lys  Leu  Thr  Arg  Thr  Asn  Gly  Ile  Thr  Tyr  Ala  Ser
          435                      440                      445
```

-continued

| | | | | | | | | | | | | | | |
|---|---|---|---|---|---|---|---|---|---|---|---|---|---|---|
| Val | Ala | Leu | Ala | Thr | Ser | Lys | Ala | Leu | Val | Lys | Phe | Asp | Pro | Glu | Ile |
| | 450 | | | | 455 | | | | 460 | | | | | |
| Ile | Gly | Pro | Arg | Asp | Ile | Ile | Lys | Ile | Ile | Glu | Ser | Lys | Thr | Ser | Glu |
| 465 | | | | | 470 | | | | 475 | | | | | 480 |
| Ala | Leu | Ala | Lys | Leu | Met | Ser | Leu | Gln | Thr | Glu | Ala | Thr | Val | Val |
| | | | | 485 | | | | | 490 | | | | | 495 |
| Thr | Leu | Gly | Glu | Asp | Asn | Leu | Ile | Ile | Arg | Glu | Glu | Val | Pro | Met |
| | | | | 500 | | | | | 505 | | | | 510 | |
| Glu | Leu | Val | Gln | Arg | Gly | Asp | Ile | Val | Lys | Val | Pro | Gly | Gly | Lys |
| | | | 515 | | | | 520 | | | | 525 | | | |
| Phe | Pro | Val | Asp | Gly | Lys | Val | Leu | Glu | Gly | Asn | Thr | Met | Ala | Asp | Glu |
| | 530 | | | | | 535 | | | | | 540 | | | | |
| Ser | Leu | Ile | Thr | Gly | Glu | Ala | Met | Pro | Val | Thr | Lys | Lys | Pro | Gly | Ser |
| 545 | | | | | 550 | | | | | 555 | | | | | 560 |
| Thr | Val | Ile | Ala | Arg | Ser | Ile | Asn | Ala | His | Gly | Ser | Val | Leu | Ile | Lys |
| | | | | | 565 | | | | | 570 | | | | | 575 |
| Ala | Thr | His | Val | Gly | Asn | Asp | Thr | Thr | Leu | Ala | Gln | Ile | Val | Lys | Leu |
| | | | 580 | | | | | 585 | | | | | 590 | | |
| Val | Glu | Glu | Ala | Gln | Met | Ser | Lys | Asn | Pro | Asn | Lys | His | Ile | Ser | Gln |
| | | | 595 | | | | | 600 | | | | | 605 | | |
| Thr | Glu | Val | Ile | Ile | Arg | Phe | Ala | Phe | Gln | Thr | Ser | Ile | Thr | Val | Leu |
| | 610 | | | | | 615 | | | | | 620 | | | | |
| Cys | Ile | Ala | Cys | Pro | Cys | Ser | Leu | Gly | Leu | Ala | Thr | Pro | Thr | Ala | Val |
| 625 | | | | | 630 | | | | | 635 | | | | | 640 |
| Met | Val | Gly | Thr | Gly | Val | Ala | Ala | Gln | Asn | Gly | Ile | Leu | Ile | Lys | Gly |
| | | | | 645 | | | | | 650 | | | | | 655 | |
| Gly | Lys | Pro | Leu | Glu | Met | Ala | His | Lys | Ile | Lys | Thr | Val | Met | Phe | Asp |
| | | | | 660 | | | | | 665 | | | | | 670 | |
| Lys | Thr | Gly | Thr | Ile | Thr | His | Gly | Val | Pro | Arg | Val | Met | Arg | Val | Leu |
| | | | 675 | | | | | 680 | | | | | 685 | | |
| Leu | Leu | Gly | Asp | Val | Ala | Thr | Leu | Pro | Leu | Arg | Lys | Val | Leu | Ala | Val |
| | | 690 | | | | | 695 | | | | | 700 | | | |
| Val | Gly | Thr | Ala | Glu | Ala | Ser | Ser | Glu | His | Pro | Leu | Gly | Val | Ala | Val |
| 705 | | | | | 710 | | | | | 715 | | | | | 720 |
| Thr | Lys | Tyr | Cys | Lys | Glu | Glu | Leu | Gly | Thr | Glu | Thr | Leu | Gly | Tyr | Cys |
| | | | | 725 | | | | | 730 | | | | | 735 | |
| Thr | Asp | Phe | Gln | Ala | Val | Pro | Gly | Cys | Gly | Ile | Gly | Cys | Lys | Val | Ser |
| | | | 740 | | | | | 745 | | | | | 750 | | |
| Asn | Val | Glu | Gly | Ile | Leu | Ala | His | Ser | Glu | Arg | Pro | Leu | Ser | Ala | Pro |
| | | | 755 | | | | | 760 | | | | | 765 | | |
| Ala | Ser | His | Leu | Asn | Glu | Ala | Gly | Ser | Leu | Pro | Ala | Glu | Lys | Asp | Ala |
| | 770 | | | | | 775 | | | | | 780 | | | | |
| Val | Pro | Gln | Thr | Phe | Ser | Val | Leu | Ile | Gly | Asn | Arg | Glu | Trp | Leu | Arg |
| 785 | | | | | 790 | | | | | 795 | | | | | 800 |
| Arg | Asn | Gly | Leu | Thr | Ile | Ser | Ser | Asp | Val | Ser | Asp | Ala | Met | Thr | Asp |
| | | | | 805 | | | | | 810 | | | | | 815 | |
| His | Glu | Met | Lys | Gly | Gln | Thr | Ala | Ile | Leu | Val | Ala | Ile | Asp | Gly | Val |
| | | | 820 | | | | | 825 | | | | | 830 | | |
| Leu | Cys | Gly | Met | Ile | Ala | Ile | Ala | Asp | Ala | Val | Lys | Gln | Glu | Ala | Ala |
| | | 835 | | | | | 840 | | | | | 845 | | | |
| Leu | Ala | Val | His | Thr | Leu | Gln | Ser | Met | Gly | Val | Asp | Val | Val | Leu | Ile |
| | 850 | | | | | 855 | | | | | 860 | | | | |
| Thr | Gly | Asp | Asn | Arg | Lys | Thr | Ala | Arg | Ala | Ile | Ala | Thr | Gln | Val | Gly |
| 865 | | | | | 870 | | | | | 875 | | | | | 880 |

```
Ile Asn Lys Val Phe Ala Glu Val Leu Pro Ser His Lys Val Ala Lys
                885             890             895

Val Gln Glu Leu Gln Asn Lys Gly Lys Lys Val Ala Met Val Gly Asp
            900             905             910

Gly Val Asn Asp Ser Pro Ala Leu Ala Gln Ala Asp Met Gly Val Ala
        915             920             925

Ile Gly Thr Gly Thr Asp Val Ala Ile Glu Ala Ala Asp Val Val Leu
    930             935             940

Ile Arg Asn Asp Leu Leu Asp Val Val Ala Ser Ile His Leu Ser Lys
945             950             955                         960

Arg Thr Val Arg Arg Ile Arg Ile Asn Leu Val Leu Ala Leu Ile Tyr
            965             970             975

Asn Leu Val Gly Ile Pro Ile Ala Ala Gly Val Phe Met Pro Ile Gly
            980             985             990

Ile Val Leu Gln Pro Trp Met Gly Ser Ala Ala Met Ala Ala Ser Ser
        995             1000            1005

Val Ser Val Val Leu Ser Ser Leu Gln Leu Lys Cys Tyr Lys Lys Pro
    1010            1015           1020

Asp Leu Glu Arg Tyr Glu Ala Gln Ala His Gly His Met Lys Pro Leu
1025             1030           1035                      1040

Thr Ala Ser Gln Val Ser Val His Ile Gly Met Asp Asp Arg Trp Arg
            1045           1050                       1055

Asp Ser Pro Arg Ala Thr Pro Trp Asp Gln Val Ser Tyr Val Ser Gln
            1060           1065           1070

Val Ser Leu Ser Ser Leu Thr Ser Asp Lys Pro Ser Arg His Ser Ala
        1075           1080                1085

Ala Ala Asp Asp Asp Gly Asp Lys Trp Ser Leu Leu Leu Asn Gly Arg
1090            1095                      1100

Asp Glu Glu Gln Tyr Ile
1105            1110
```

WILSON'S DISEASE GENE

The invention disclosed herein was made with Government support under NIH Grant No. NS28877 and HG00462 from the Department of Health and Human Services. Accordingly, the U.S. Government has certain rights in this invention.

BACKGROUND OF THE INVENTION

Throughout this application, various references are referred to within parenthesis. Disclosures of these publication in their entireties are hereby incorporated by reference into this application to more fully describe the state of the art to which this invention pertains. Full bibliographic citation for these references may be found at the end of each series of experiments in the Experimental Details section.

Wilson's disease (WD) is an autosomal recessive disorder of copper metabolism with a world-wide prevalence of 30 per million and a corresponding carrier frequency of 1 in 90. Biochemically it is characterized by abnormally high concentrations of copper in a number of organs and tissues, and deficiency of the plasma copper-protein, ceruloplasmin. The excess copper causes damage to the liver and brain. In the former, acute and chronic hepatic disease progresses to cirrhosis; in the latter motor and psychiatric disturbances reflect the cerebral pathology. Clinical onset may occur in the latter half of the first decade, is most frequent in adolescence, and was delayed in two patients until the seventh decade. Untreated, the disease is always fatal but pharmacologic removal or detoxification of the excess copper is prophylactic in the asymptomatic patient and can be dramatically effective therapy for patients with hepatic or cerebral symptomatology. The mechanism by which the abnormal gene disturbs copper homeostasis is unknown (1).

In 1985, genetic linkage studies showed that the Wilson's disease locus segregates with the red cell enzyme esterase-D (ESD) on chromosome 13(2). Subsequent linkage analyses limited the disease locus to a genomic region bracketed by the DNA marker loci D13S31 and D13S59, although the odds for a disease locus in the adjacent interval between loci D13S31 and D13S25 were estimated to be only seven times less likely (3).

BRIEF DESCRIPTION OF THE FIGURES

FIG. 2A–G Pattern hybridization to construct cosmid contigs. Each of the 283 "positive" cosmids was radiolabelled at both ends using the Riboprobe method (see Methods) and hybridized simultaneously to an ordered array blot containing the same 283 cosmids. For example, frame (A) shows the 3a3 cosmid end-clone mixture identifying itself (arrow) and clones 3a4, 2a2 and 5b3. The configuration of cosmid overlap is illustrated at the bottom of the figure. Order was determined in larger contigs with the assistance of a tree-building algorithm (5, 6).

FIG. 5A–5H DNA sequence of pWD and translated amino-acid sequence. Shadow regions correspond to the transmembrane helices. Square boxes represent consensus sequences found in related ATPase proteins, including: metal ending sites 1–5, phosphatase/transduction domain; phosphorylation site; and nucleotide binding site and hinge domain. Shadowed dinucleotide sequences correspond to sequences missing in the Mc1 (Menkes) gene, respectively 2, 4, 4, 3, 18 and 1 amino acid residue. Striped dinucleotide sequences correspond to additional sequences found in the Mc1 gene, respectively 179, 45, 11 and 6 residues.

FIGS. 6A–D Consensus regions found in the most homologous proteins using the BLAST program (12 of the second series of experiments). Shadow lines indicate conserved residues whereas stars indicate strongly homologous residues. Dots, above the sequences are plotted every ten residues. The database, protein name, and access numbers corresponding to proteins lited in the figure are as follows: SWISSPROT: K+ATPase (E. Faecalis). P05425; Cd ATPase, P20021; Fixl, P18398; K+ATPase (*E. Coli*), P03960; H+ATPase 1, P05030; E1–E2 ATPase 1A, P11718; H+ATPase2, P28876; Mg++ATPase, P22036; E1–E2 ATPase P07893; Hg++reductase, P08662; Hg++transport protein, P13113. GENBANK: Mc1, L06133; CopA, L13292; ATPaseS.C., J04421; Ca++ATPase, M83363; CadA, L10909; NR1 Hg++resistance, K03089; Hg++resistance, L04303. PIR: H+/K+ATPase, D42707, Hypothetical protein 3, S18588.

FIG. 8A Kyle and Doolittle hydrophobicity plot, and FIG. 8B Profile of positive and negative charges (see 18 of the second series of experiments).

FIG. 9 Site of the Wilson's disease mutation. Sequence conservation unique to heavy-metal binding P-type ATPases is shown (34 of the second series of experiments). The H (histidine) residue at position 714 is transverted to glutamine in a predicted 25%–30% of WD chromosomes from the U.S. and Russian clinical samples (6). The CPC residues are located in the transmembrane region, 7 amino acid residues 5' to the single proline (P), which is likewise 34 amino acids 5' to the DKTG motif. The histidine is located another 39 amino acids 3' from the DKTG motif.

DETAILED DESCRIPTION OF THE INVENTION

Figure 1:
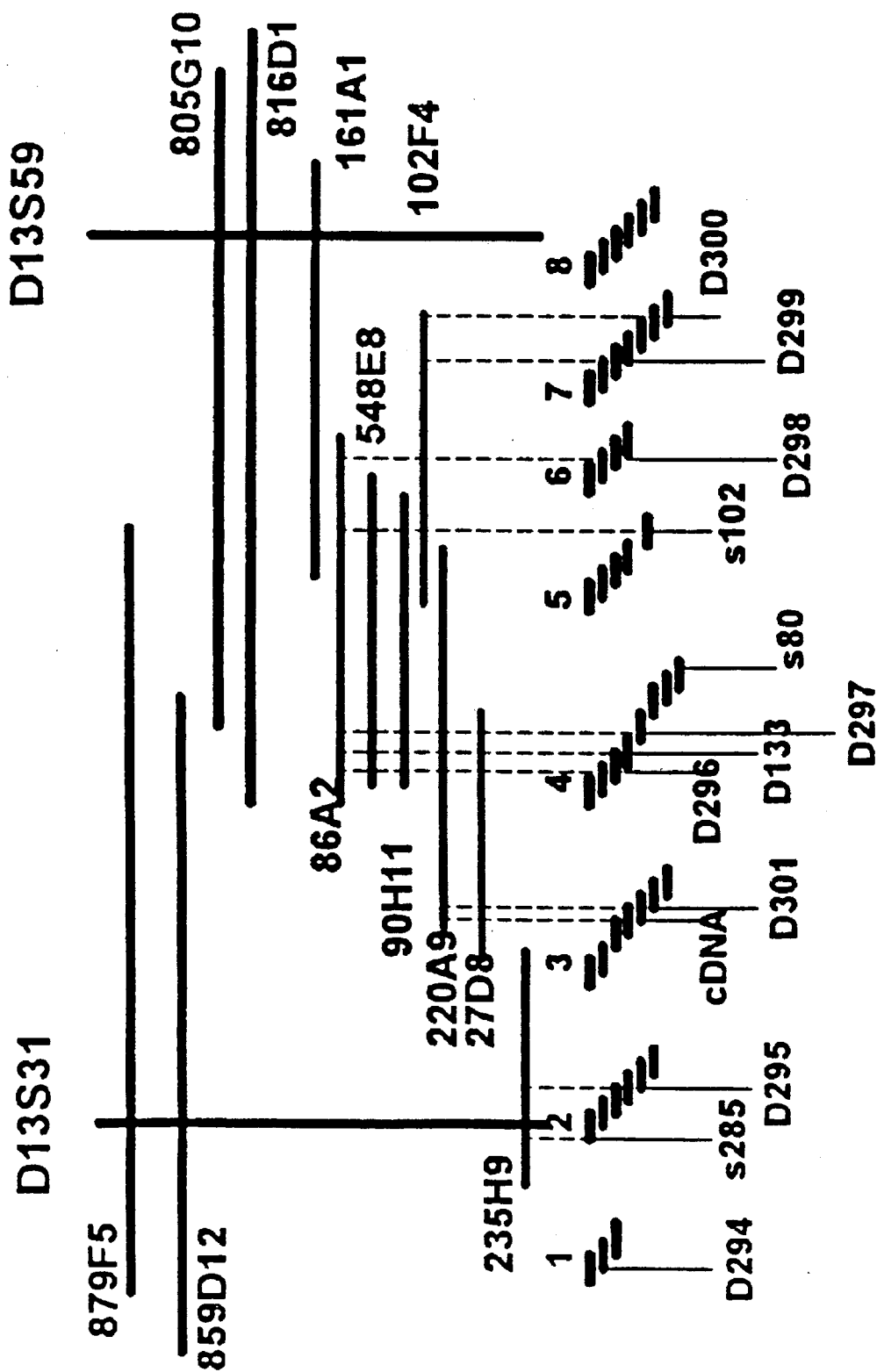
FIG. 1 Physical Map of the Wilson's disease region Loci D13S31 is the centromeric flanking marker and D13S59 the telomeric flanking marker for the WD locus (3). The top four horizontal lines represent large-insert YAC clones (15). The 8 mid-size YAC clones are from a chromosome 13-enriched sublibrary (5) selected from the CEPH I genomic YAC library (4). At the bottom of the figure are the minimum number of overlapping cosmid clones which span each island. Microsatellite markers are shown at the bottom of the figures along with several sequence tag site (STS) sequences and a WD candidate cDNA clone. Cosmid and YAC clones bearing he microsatellite and STS sequences are identified by the intersection of vertical and horizontal lines. The large-insert YAC clones (and 161A1) were not typed for the PCR markers. Clone nomenclature corresponds to the original libraries. Primer pairs and heterozygosity values for the new microsatellite markers are as follows: D13S294 (0.82)-CCCAGTGAGCAGCCTCTAAA (SEQ ID No. 3) and AACAGAAATCAGGCCAGTGTG (SEQ ID No. 4); D13S295 (0.68)-CTGCCACCTATTTTTGTAAATAAAG (SEQ ID No. 5) and TGATCTGGTGGTTCAACTGG (SEQ ID No. 6); D13S301 (0.77)-ATCATACCTGGTTGTG-CAACC (SEQ ID No. 7) and CCAGATGCT-TCTTTCTAAACACACA (SEQ ID No. 8); D13S296 (0.77) CAAACTTTTAGTATGAGTCTATCTCTCTCT (SEQ ID No. 9) and TCATTAAAGTGAGGAGTGAGGTAAATG (SEQ ID No. 10); D13S197 (0.69)-TTATGAT-GAAAAAAGTAATATAAGAGGTCCC (SEQ ID No. 11) and AGCTGTATCTGGGGTTGG (SEQ ID No. 12); D13S298 (0.72)-AGTTTCTACATGAATAAAATCGTAC-TAGAAG (SEQ ID No. 13) and GGTATCTTGTATAATAC-TACCTTCCATCA (SEQ ID No. 14); D13S299 (0.79)-TTTAACTGGCATGTTAATCTGGG (SEQ ID No. 15) and CTCCCCCTCCTTGCCTGCAACT (SEQ ID No. 16); D13S300(0.76)-CCTGGAACTGGAAGATGGCA (SEQ ID No. 17) and GGAGTTGGGGAGADCCACAAT (SEQ ID No. 18).

This invention provides an isolated, vertebrate nucleic acid molecule encoding the normal polypeptide which prevents development of Wilson's disease.

In an embodiment, the nucleic acid molecule is DNA. In a further embodiment, the DNA is a cDNA. In another further embodiment, the DNA is genomic DNA.

In another embodiment of this invention, the nucleic acid molecule is RNA.

In a preferred embodiment, the above described nucleic acid molecule is encoding a human polypeptide which prevents development of Wilson's disease.

This invention also encompasses DNAs and cDNAs which encode amino acid sequences which differ from the polypeptide which prevents development of Wilson's disease, but which should not produce phenotypic changes. Alternatively, this invention also encompasses DNAs and cDNAs which hybridize to the DNA and cDNA of the subject invention. Hybridization methods are well known to those of skill in the art.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

This invention also provides a nucleic acid molecule comprising a nucleic acid molecule of at least 15 nucleotides capable of specifically hybridizing with a sequence included within the sequence of the above-described nucleic acid molecule. This molecule may either be a DNA or RNA molecule.

This nucleic acid molecule produced can either be DNA or RNA. As used herein, the phrase "specifically hybridizing" means the ability of a nucleic acid molecule to recognize a nucleic acid sequence complementary to its own and to form double-helical segments through hydrogen bonding between complementary base pairs.

This nucleic acid molecule of at least 15 nucleotides capable of specifically hybridizing with a sequence of a nucleic acid molecule encoding the normal polypeptide which prevents the development of Wilson's disease can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes a polypeptide which prevents the development of Wilson's disease into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the above-described DNA molecule downstream of a bacteriophage promoter such as T3, T7 or SP6. Large amounts of RNA probe may be produced by incubating the labeled nucleotides with the linearized fragment where it contains an upstream promoter in the presence of the appropriate RNA polymerase.

These probes are useful for detecting the expression of Wilson's disease gene. These probes are also useful for "in situ" hybridization to locate tissues which express this gene, or for other hybridization assays for the presence of this gene or its mRNA in various biological tissues.

This invention further provides the above-described isolated, vertebrate nucleic acid molecule operatively linked to a promoter of RNA transcription.

The isolated above-described isolated nucleic acid molecule can be linked to different vector systems. Various vectors including plasmid vectors, cosmid vectors, bacteriophage vectors and other viruses are well known to ordinary skilled practitioners. This invention further provides a vector which comprises the isolated nucleic acid molecule encoding for the normal polypeptide which prevents the development of Wilson's disease.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

In an embodiment, the above-described molecule is cloned in a plasmid. This plasmid is designated pWD 5'-191 (See FIG. 3). An 0.85 kb insert can be cut out from the 2.9 kb vector by double digestion with NotI and SfiI. Plasmid pWD5'-191 was deposited on Sep. 1, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid,pWD 5'-191, has been accorded ATCC Accession Number 75544.

In another embodiment, the above-described molecule is cloned in a plasmid. This plasmid is designated pWD3'-1 (See FIG. 3). The size of the linear plasmid after cutting with NotI is 4.8 kb. This plasmid pWD3'-1 was deposited on Sep. 1, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid pWD3'-1 has been accorded ATCC Accession Number 75546.

In still another embodiment, the above-described molecule is cloned in a plasmid. This plasmid is designated pWD3'-3 (See FIG. 3). The size of the linear plasmid after cutting with NotI is 5.36 kb. Plasmid, pWD3'-3 was deposited on Sep. 1, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid, pWD3'-3, was accorded ATCC Accession Number 75545.

In an embodiment, the above-described molecule is cloned in a plasmid. This plasmid is designated pWD02 (See FIG. 3). A 3.5 kb insert can be cut out from the 2.9 kb vector by digestion with NotI. This plasmid pWD02 was deposited on Sep. 1, 1993 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. Plasmid pWD02 was accorded ATCC Accession Number 75543.

This invention further provides a host vector system for the production of a polypeptide having the biological activity of the normal development polypeptide which prevents Wilson's disease. These vectors may be transformed into a suitable host cell to form a host cell vector system for the production of a polypeptide having the biological activity of the normal polypeptide which prevents the development of Wilson's disease.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the polypeptide which prevents the Wilson's disease.

This invention further provides an isolated DNA or cDNA molecule described hereinabove wherein the host cell is selected from the group consisting of bacterial cells (such as *E. coli*), yeast cells, fungal cells, insect cells and animal cells. Suitable animal cells include, but are not limited to Vero cells, HeLa cells, Cos cells, CV1 cells and various primary mammalian cells.

This invention provides a mammalian cell comprising a DNA molecule encoding a polypeptide which prevents Wilson's disease, such as a mammalian cell comprising a plasmid adapted for expression in a mammalian cell, which comprises a DNA molecule encoding a polypeptide which prevents Wilson's disease and the regulatory elements necessary for expression of the DNA in the mammalian cell so located relative to the DNA encoding a polypeptide which prevents Wilson's disease as to permit expression thereof.

Numerous mammalian cells may be used as hosts, including, but not limited to, liver stem cells, the mouse fibroblast cell NIH3T3, CHO cells, HeLa cells, Ltk⁻ cells, Cos cells, etc. Expression plasmids such as that described supra may be used to transfect mammalian cells by methods well known in the art such as calcium phosphate precipitation, electroporation or DNA encoding the polypeptide which prevents the development of Wilson's disease may be otherwise introduced into mammalian cells, e.g., by microinjection, to obtain mammalian cells which comprise DNA, e.g., cDNA or a plasmid, encoding a polypeptide which prevents the development of Wilson's disease.

This invention also provides a method of producing a polypeptide which prevents development of Wilson's disease which comprises growing the above-described host vector system under suitable conditions permitting production of the polypeptide and recovering the polypeptide so produced.

This invention also provides a polypeptide encoded by the above-described isolated, vertebrate nucleic acid molecule.

This invention also provides an antibody capable of binding to polypeptide encoded by the above-described nucleic acid molecule. In an embodiment, the antibody is a monoclonal antibody.

Polyclonal antibodies against the polypeptides may be produced by immunizing animals using the polypeptie which prevents development of Wilson's disease, produced by the above method. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of the polypeptide which prevents the Wilson's disease in living animals, in humans, or in biological tissues or fluids isolated from animals or humans.

Synthetic peptides corresponding to different region of the polypeptide which prevents development of Wilson's disease may be made and they may be used as antigens to generate both polyclonal and monoclonal antibodies capable of binding to the polypeptide.

This invention provides a method for diagnosing Wilson's disease in a subject comprising: (a) obtaining nucleic acid sample from the subject; (b) reverse-transcribing the RNA to cDNA if the obtained nucleic acid from step (a) is RNA; (c) cleave the DNA sample into fragments; (d) separating the DNA fragments by size fractionation; (e) hybridizing the DNA fragments with a nucleic acid molecule comprising a nucleic acid molecule of at least 15 nucleotides capable of specifically hybridizing with a sequence included within the sequence of the nucleic acid molecule encoding the normal polypeptide which prevents development of Wilson's disease, produced by the above method; and (f) comparing the detected DNA fragment from (d) with the DNA fragment from a known normal subject, the difference in size of the fragments indicating the occurrence of Wilson's disease in the subject.

One approach for performing molecular diagnosis is by allele-specific oligomer (ASO) hybridization (Kerem et al., (1989) *Science*, vol. 245:1073–1080). This approache can be used for molecular diagnosis of Wilson's disease because the Wilson's disease gene is now disclosed.

This invention also provide the above method for diagnosing Wilson's disease in a subject, further comprising amplification of the DNA obtained after step (b) by PCR technology.

PCR technology has been well-known to an ordinary skilled artisan. U.S. Pat. No. 4,683,202 by Mullis discloses a process for amplifying any desired specific nucleic acid sequence contained in a nucleic acid or mixture therof using PCR technology. The content of U.S. Pat. No. 4,683,202 is incorporated in here by reference.

In an embodiment of the above method, the DNA sample is cleaved by restriction enzyme.

This invention further provide the above method, wherein the size fractionation is step (d) is effected by a polyacrylamide or agarose gel.

In an embodiment, the nucleic acid molecule is labeled with a detectable marker. In a further embodiment, the detectable marker is a radiolabelled molecule, a fluorescent molecule, an enzyme, or a ligand.

This invention further provides the above; method further comprising transferring the DNA fragments into a solid matrix before step (e).

This invention also provides a method for diagnosing Wilson's disease in a subject comprising: (a) obtaining RNA sample from the subject; (b) separating the RNA sample into different species by size fractionation; (c) hybridizing the RNA species with a nucleic acid molecule comprising a nucleic acid molecule of at least 15 nucleotides capable of specifically hybridizing with a sequence included within the sequence of the nucleic acid molecule encoding the normal polypeptide which prevents development of Wilson's disease, produced by the above method; and (d) comparing the detected RNA species from step (c) with the RNA species from a known normal subject, the difference in size of the species indicating the occurrence of Wilson's disease in the subject.

In an embodiment, the size fractionation in step (b) is effected by a polyacrylamide or agarose gel. In another embodiment, in step (c), the nucleic acid molecule is labeled with a detectable marker. In a further embodiment, the detectable marker is a radiolabelled molecule, a fluorescent molecule, an enzyme, or a ligand.

This invention further provides the above method further comprising transferring the RNA species into a solid matrix before step (c).

This invention provides a method for diagnosing Wilson's disease in a subject comprising: (a) obtaining nucleic acid sample from the subject; (b) amplifying the nucleic acids; (c) separating and analyzed the amplified nucleic acids obtained in step (b) by single-stranded conformational analysis (SSCPA) to determine the occurrence of Wilson's disease in the subject.

Orita et al. reported that single base substitutions in short DNA segments (up to about 250 bp) can be detected as shifts in electrophoretic mobility (19, 20). The base substitution causes the DNA segment to assume a unique folded conformation, which alters its mobility on a non-denaturing gel compared to the corresponding unmutated DNA segment. The strategy is to amplify the desired segment of a gene by the PCR (21), and then to compare the migration pattern of the denatured DNA with that of a reference segment of known sequence. The "single strand conformational polymorphism" (SSCP) assay is simple, rapid, and sensitive, and has now been used for detection of point mutations in several :studies (22, 23, 24, 25, 26). The SSCP can be applied to both DNA or RNA samples.

This invention provides the above method further comprising synthesizing cDNA copy of the nucleic acid if the nucleic acid sample is RNA.

In an embodiment, the nucleic acid is amplified by PCR technology.

This invention also provides a pharmaceutical composition comprising the polypeptide which is encoded by the above-described isolated, vertebrate nucleic acid molecule which encodes the normal protein that prevents development of Wilson's disease effective to reduce the symptom of Wilson's disease and a pharmaceutically acceptable carrier.

For the purpose of this invention, "pharmaceutically acceptable carrier" means any of the standard pharmaceutical carriers. Examples of suitable carriers are well-known in the art and may include, but not limited to, any of the standard pharmaceutical vehicles such as a phosphate buffered saline solution, phosphate buffered saline containing Polysorb 80, water, emulsions such as oil/water emulsion and various types of wetting agents.

This invention provides a method for reducing the symptom of Wilson's disease in a subject which comprises replacing the subject's Wilson's disease gene with the above-described nucleic acid molecule which encodes the normal protein that prevents development of Wilson's disease so as to reduce the symptom of Wilson's disease.

"Gene therapy" approach is well known to people in the field. With the discovery of the normal Wilson's disease gene, the mutated disease gene can be replaced by this normal gene.

Finally, this invention also provides a transgenic nonhuman mammal which comprises the isolated nucleic acid molecule encoding a polypeptide which prevents development of Wilson's disease. This invention further provides a transgenic nonhuman mammal whose genome comprises antisense DNA complementary to DNA encoding a polypeptide which prevents development of Wilson's disease so placed as to be transcribed into antisense mRNA complementary to mRNA encoding the polypeptide which prevents development of Wilson's disease and which hybridizes to mRNA encoding the polypeptide which prevents development of Wilson's disease thereby reducing its translation.

One means available for producing a transgenic animal, with a mouse as an example, is as follows: Female mice are mated, and the resulting fertilized eggs are dissected out of their oviducts. The eggs are stored in an appropriate medium such as M2 medium (16). DNA or cDNA encoding a polypeptide which prevents development of Wilson's disease is purified from a vector by methods well known in the art. Inducible promoters may be fused with the coding region of the DNA to provide an experimental means to regulate expression of the transgens. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a piper puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Another approach is to generate "knock out" transgenic mouse where the Wilson's disease gene is rendered nonfunctional. DeChiara, T. M. et al. (1991), *Cell*, vol. 64:849–859, discloses this general approach via stem cells. First, the Wilson's disease gene of the mouse stem cell will be altered so that it will no longer be functional. Second, the stem cell with the "knock out" gene will be introduced to the blastocyte and the mouse developed will be a "knock out" mouse.

This invention will be better understood from the Experimental Details which follow. However, one skilled in the art will readily appreciate that the specific methods and results discussed are merely illustrative of the invention as described more fully in the claims which follow thereafter.

Experimental Details

Materials and Methods

Library Screening Chromosome 13-specific cosmid library

A flow-sorted, arrayed chromosome 13 cosmid library was obtained from Los Alamos Laboratories (N. Brown, J. Longmire, and L. Deaven). The 16,896 clone library was arrayed on 11 Hybond N+ (Amersham) nylon membranes, each with 1536 clones.

Chromosome 13-specific CEPH I YAC library

The 52,800 clone Centre d'Etude Polymorphism Humain (CEPH) I YAC library (4) (average insert size, 300–400 kb) was screened with hybridization probes prepared by inter-Alu PCR amplification (10) of the monochromosomal 13 cell hybrid, GM10898. 1421 clones Were identified, 86% of which were shown by in situ hybridization to contain chromosome 13DNA sequences (5).

Chromosome 13-specific CEPH II YAC library

The large insert CEPH library (400–1200 kb) was likewise screened with inter-Alu PCR probe (I. Chumakov, unpublished; 5) to identify 819 CH13 enriched YAC clones. Replicate copies of the two YAC sublibraries were used to map the WD gene region. High density colony filters were prepared with a Biomek™ 1000 Automated Laboratory Workstation (Beckman). YAC and cosmid colony filters were grown and hybridized as described (5).

Inter-Alu PCR

Primers alu 1:5'-GGA TTA CAG GYR TGA GCC A (SEQ ID No. 1) -3' and alu 2:5'-RCC AYT GCA CTC CAG CCT G (SEQ ID No. 2) 3' (R=purines; Y=pyrimidines) were added to a final concentration of 1 µM each together with 1 ng/100 ul yeast (YAC) DNA as described (5). The PCR products were purified and concentrated to 50–100 ng/µl with a Centricoh 100 microconcentrator (Amicon) or MagicPCR Prep Kit (Promega).

Construction of Cosmid Contigs

Cosmid DNA was isolated from 5 ml overnight cultures as described (5). 1 ug of each cosmid DNA was incubated with T3 and T7 RNA polymerase, pre-annealed with denatured human placental DNA, and hybridized to cosmid colony filters as described (5). Clones identified by hybridization to cosmid riboprobe pairs were entered into a database and contigs were constructed by a tree-building algorithm (5, 6).

Identification of microsatellite markers

Dinucleotide repeat sequence markers were developed directly from cosmid clones as described previously (7). Allele frequencies were determined from the "normal chromosomes" identified in each of 128 parent-affected child combinations in three different populations.

Calculation of linkage disequilibrium

To test whether a single allele is significantly more frequent on "Wilson disease chromosomes" than on normal chromosomes, standardized linkage disequilibrium coefficient (D/DMax) (8) and Yule's association coefficient (9) were calculated for each allege detected by each microsatellite marker. Significance of association for the alleles showing the largest disequilibrium coefficient was evaluated using a one-sided chi-square test corrected for multiple testing by multiplying the corresponding p value by the number of alleles observed in the microsatellite marker.

Clinical sample

The Sardinian cohort, drawn from 42 unrelated and non-consanguineous families, consisted of 158 individuals comprised of 57 WD patients, 62 parents and 39 unaffected siblings. The Russian cohort, drawn from 18 unrelated families, consisted of 66 individuals comprised of 24 WD patients, 36 parents and 6 unaffected siblings. In one family, where parents were first cousins, only one WD chromosome was included in the marker allege and haplotype analyses. The American cohort, drawn from 50 unrelated families, consisted of 125 individuals comprised of 50 WD patients, 70 parents, and 5 unaffected siblings. Two sets of parents were first cousins. Families in the American sample were from 13 states, Puerto Rico (three), Greece (one) and India (one). In 13 families, both parents were Jewish. The number of WD chromosomes analyzed (by at least one marker) from the Sardinian, Russian, and American cohorts were 82, 35, and 110 respectively. Five families from Sicily were analyzed including 6 parents and 5 WD patients. Diagnosis of Wilson's disease in the American families was based upon the criteria described by Scheinberg and Sternlieb (1).

Experimental Results

Wilson's disease (WD) is an autosomal recessive disorder of copper metabolism with an estimated worldwide carrier frequency of 1 in 90. Genetic linkage analysis has defined a 1–2 cM region at 13q14.3 which contains the disease locus. A novel rapid physical mapping strategy was used to construct complete YAC contigs and islands of cosmid contigs across the disease gene region. Development of microsatellite markers directly from cosmid clones identified physically ordered, highlypolymorphic markers at approximately 10-fold higher resolution than is possible by genetic analysis. The dense collection of markers were used to analyze 50 American, 42 Sardinian, 18 Russian, and 5 Sicilian Wilson's disease families. Linkage disequilibrium analysis identified a DNA marker interval very likely to harbor the disease locus and haplotype analysis indicates a high degree of allelic heterogeneity among WD cases. In the American families, a few predominant haplotypes account for roughly half of allWD chromosomes, the remaining haplotypes occur with relatively low frequency. In the more homogeneous Sardinian population, three haplotypes account for approximately 80% of WD chromosomes. The data indicate that approximately 50% of WD mutations will occur with very low frequency in the American and Russian populations. The physical mapping protocol described here is well-suited for the rapid generation of microsatellite markers at approximately 100 kb intervals across a genomic region defined by flanking DNA markers. Such dense microsatellite maps provide a powerful tool for genetic analysis of heritable loci.

Physical Mapping and cloning of the WD Gene Region

A 4.3 kb insert from the WD flanking marker D13S31 (probe pCR1324) was used to screen the large insert, CEPH II YAC sublibrary (see Methods; 5). Clones 879F5 (1.3Mb) and 859D12 (1.4 Mb) were identified (FIG. 1). A chromosome "walk" was performed using radiolabeled inter-Alu PCR product (10) from both YAC clones to re-screen the CEPH II library. Among the positive clones identified, YACs 805G10 (1.2 Mb) and 816D1(1.6 Mb) contain homologous sequence to the distal WD flanking marker, D13S59 (data not shown). A higher resolution YAC map was constructed using inter-Alu PCR product from the 4 large YAC clones shown in FIG. 1 to screen the 1431 colony CEPH I YAC sublibrary (see Methods). A total of 16 mid-size YACs were identified, eight of which are shown in FIG. 1. The pattern of mid-size YACs detected by each large YAC clone was used to order the smaller YAC clones relative to one another. Inter-Alu PCR "fingerprinting" of YAC clones further assisted the ordering process (data not shown). The YAC clones have not been characterized for the presence of chimeric (non- CH13) DNA sequence because they were used to screen a flow-sorted, CH13 enriched cosmid library. This strategy rendered the chimeric DNA "invisible" because these segments are not represented in the CH13-specific cosmid library.

Inter-Alu PCR probes from all 8 midsize YACs were combined to screen a CH13-specific cosmid library (see Methods). 283 "positive" cosmids were identified. To align the cosmids into contigs, 283 high density filters were prepared each containing a full array of the 283 positive cosmids. Radiolabelled RNA end-probes were generated from each of the 283 cosmids using the T3 and T7 promoters flanking the cosmid inserts and the "riboprobe" labeling system (Stratagene®) (5). In a single experiment, 283 end-probe preparations were hybridized to 283 high density filters. FIG. 2 illustrates the contig building procedure. Each cosmid that forms part of a contig identifies itself and its overlapping neighbors. Somewhat less than 20% of clones hybridized only to themselves, indicating either that they were false positives, or form contigs of one. The seven cosmid contigs identified by this method, and verified by subsequent tests (excluding contig 3), consisted of 5–44 cosmids and are estimated to span 100 to 600 kb each. An eighth cosmid contig was identified using a candidate cDNA clone for the WD gene (11). PCR primers from the clone amplified regions of YACs 220A9 and 27D8, but did not amplify cosmids from the 7 contigs. The 3.5 kb cDNA clone was used to screen the entire cosmid library. A total of 16 overlapping cosmids were identified (a minimum of 7 cosmids span contig 3, FIG. 1).

Mid-size YAC DNAs were separated by pulsed filed gel electrophoresis (12), extracted from agarose, partially purified with Gene-clean (Bio 101, Inc.), and radiolabelled to hybridize against cosmid arrays from the 8 cosmid contigs (data not shown). The pattern of cosmid hybridization was used to order cosmid islands across the disease gene region. Fluorescent in situ hybridization of individual cosmid clones was used to eliminate several "questionable" smaller cosmid islands (13 ). At least one cosmid from each contig was chosen to isolate microsatellite DNA markers (7) and STS sequences. PCR amplification of cosmid and mid-size YAC clones with oligonucleotide primers from the DNA markers and STS sequences verified the physical order of cosmid contig islands (FIG. 1). Eight new microsatellite markers and one previously mapped marker, D13S133 (7), are spaced at estimated distances of 100–200 kb across the disease gene region.

Linkage Disequilibrium Analysis

A total of 15 Wilson's disease families representing diverse ethnic and geographical populations were genotyped with the nine microsatellite markers described above. In each family, the two chromosomes (haplotypes) inherited by an affected child constitute the "WD" chromosomes, and the remaining two chromosomes (haplotypes) constitute the "normal" chromosomes. Table I summarizes the distribution of DNA marker alleles in each of the three clinical samples (S=Sardinian; R=Russian; A=American). Significant LD to the disease locus was detected with 7 of 9 DNA markers in the relatively homogeneous Sardinian sample. In the more heterogeneous American sample, the strongest evidence of LD was detected at loci D13S295 and D13S296. This result is interesting because these loci flank a candidate gene for Wilson's disease (11) ("cDNA" in FIG. 1). A single base pair C→A transversion within the candidate gene was not detected in over 100 normal chromosomes and associates preferentially with the most common WD haplotype (aA/rA; see discussion below) in the Russian and American families (11). Marker D13S301, located to the same cosmid clone as the cDNA clone, detects significant LD only in the Sardinian families presumably because the "5" allele is the most common allele on both normal and WD chromosomes. Thus, LD data strongly suggests the WD gene resides between loci D13S295 and D13S296, possibly at the candidate gene locus.

TABLE I

| Locus D13 | Pop[1] | # Chrom[2] WD | N | Alleles Total | WD[3] | N[4] | D/Amax | /A/[5] | p[6] |
|---|---|---|---|---|---|---|---|---|---|
| S294 | S | 78 | 59 | 10 | 6 | 4 | 0.43 | 0.51 | NS |
|  | R | 31 | 32 | 9 | 6 | 9 | 1 | 1 | NS |
|  | A | 93 | 62 | 13 | 13 | 4/9 | 0.50 | 0.52 | NS |
| S295 | S | 76 | 58 | 5 | 3 | 1 | 0.23 | 0.25 | NS |
|  | R | 32 | 33 | 4 | 2 | 4 | 0.44 | 0.53 | NS |
|  | A | 99 | 70 | 7 | 2 | 4 | 0.84 | 0.87 | *** |
| WDC[7] | A | 26 | 102 | 2 | A | C | 1.0 | 1.0 | *** |
| S301 | S | 82 | 61 | 10 | 5 | 5 | 0.30 | 0.55 | * |
|  | R | 33 | 32 | 10 | 5 | 5 | 0.30 | 0.46 | NS |
|  | A | 99 | 72 | 12 | 5 | 5 | 0.20 | 0.33 | NS |

TABLE I-continued

| Locus | | # Chrom[2] | | Alleles | | | | | |
|---|---|---|---|---|---|---|---|---|---|
| D13 | Pop[1] | WD | N | Total | WD[3] | N[4] | D/Amax | /A/[5] | p[6] |
| S296 | S | 80 | 61 | 6 | 10 | 5 | 0.39 | 0.65 | *** |
|  | R | 35 | 35 | 7 | 9 | 5 | 0.85 | 0.89 | * |
|  | A | 99 | 73 | 9 | 9 | 10 | 0.87 | 0.83 | *** |
| S133 | S | 82 | 61 | 14 | 14 | 14 | 0.34 | 0.58 | * |
|  | R | 33 | 34 | 12 | 14 | 14 | 0.32 | 0.53 | NS |
|  | A | 96 | 69 | 14 | 14 | 14 | 0.26 | 0.47 | NS |
| S297 | S | 82 | 58 | 6 | 3 | 4 | 0.82 | 0.92 | *** |
|  | R | 33 | 34 | 4 | 4 | 4 | 0.07 | 0.10 | NS |
|  | A | 97 | 68 | 9 | 4 | 4 | 0.23 | 0.39 | NS |
| S298 | S | 78 | 58 | 8 | 3 | 3 | 0.31 | 0.53 | ** |
|  | R | 35 | 36 | 8 | 7 | 3 | 0.11 | 0.16 | NS |
|  | A | 101 | 71 | 10 | 3 | 7 | 0.39 | 0.56 | ** |
| S299 | S | 78 | 61 | 10 | 8 | 16 | 0.61 | 0.81 | *** |
|  | R | 35 | 36 | 10 | 16 | 16 | 0.15 | 0.26 | NS |
|  | A | 95 | 66 | 12 | 16 | 16 | 0.28 | 0.44 | NS |
| S300 | S | 78 | 59 | 9 | 8 | 3 | 0.81 | 0.89 | *** |
|  | R | 31 | 30 | 6 | 2 | 9 | 0.35 | 0.54 | NS |
|  | A | 97 | 70 | 12 | 2 | 3 | 0.40 | 0.47 | NS |

Table I: Evaluation of allelic allocation in Wilson's disease families
1) The populations listed are: S = Sardinian; R = Russian; and A = American.
2) Number of Wilson's (WD) and normal (N) chromosomes genotyped.
3) allele with the largest positive deviation between observed frequency and frequency expected under the hypothesis of no association (8).
4) allele with the highest frequency in normal chromosomes.
5) Yules association coefficient (9).
6) p values for chi-square test of association with Yates correction for continuity and correction for number of alleles; * = p < 0.01;  = p < 0.001; * = p < 0.0001.
7) Wilson's disease candidate gene.

Table II shows the common haplotypes in each of the three large clinical samples. In the Sardinian population, a single 7-marker haplotype (sA) was found in 26 chromosomes (36% of all WD chromosomes). Another 21 chromosomes differed from sA at a single marker locus. Overall, 47 WD chromosomes (65%) carried a six-marker "sA" haplotype as shown in Table II. The same 6-marker haplotype was never found in 57 unambiguously genotyped normal chromosomes, and only three normal chromosomes carried a 5-marker haplotype "sA". Assuming that the 2 bp differences in a single microsatellite marker are due to microsatellite instability (14), the strong association between WD and the 6-marker "sA" haplotype (chi-square=55.75, p<0.000001) suggests that all 6-marker "sA" haplotype WD chromosomes carry the same WD mutation. This mutation presumably derived from a single mutation event which occurred on the haplotype "sA" chromosome. In the Sardinian population, two remaining haplotypes (sB, sC) account for an additional 11 WD chromosomes. All other WD haplotypes differ from each other at two or more marker loci.

TABLE II

| Locus | Sardinian | | | Russian | | | American | | | | | |
|---|---|---|---|---|---|---|---|---|---|---|---|---|
| D13 | sA | sB | sC | rA | rB | rC | aA | aB | aC | aD | aE | aF |
| S294 | — | — | — | — | — | — | — | — | — | — | — | — |
| S295 | — | — | — | 2 | 3 | 3 | 2 | 1 | 1 | 4 | 4 | 4 |
| S301 | 5 | 10 | 2 | 5 | 4 | 6 | 5 | 5 | 6 | 5 | 5 | 6 |
| S296 | 10 | 5 | 5 | 9 | 5 | 5 | 9 | 10 | 10 | 10 | 9 | 10 |
| S133 | 14 | 5 | 4 | 14 | 5 | — | 14 | 14 | 14 | 14 | 14 | 14 |
| S297 | 3 | 7 | 4 | 4 | 7 | 7 | 4 | 4 | 3 | 3 | 3 | 4 |
| S298 | 3 | 7 | 3 | 3 | 7 | 7 | 3 | 3 | 7 | 5 | 3 | 4 |
| S299 | 8 | 5 | 16 | — | — | — | — | — | — | — | — | — |
| S300 | 8 | 9 | 9 | — | — | — | — | — | — | — | — | — |
| WD (#) | 47 | 8 | 3 | 8 | 4 | 2 | 22 | 5 | 3 | 4 | 2 | 2 |
| (%) | (65) | | | (26) | | | (29) | | | | | |
| N (#) | 0 | 2 | 2 | 1 | 2 | 0 | 0 | 3 | 1 | 0 | 2 | 0 |
|  | | 81% | | | 52% | | | | 50% | | | |

Table II Common haplotypes detected in the Sardinian, Russian, and American samples. Total haplotypes for each column indicate all WD chromosomes from that clinical sample which match the haplotype exactly, or which differ by one marker genotype due to unknown phase, untyped marker, or 2 bp difference at one marker locus. Percent of total chromosomes indicates the percent of WD chromosomes in a particular clinical sample (Sardinian, Russian, or American). Markers which show no genotype were relatively more divergent from the other loci in that population, presumably reflecting historical recombination.

The predominant haplotype identified among the American and Russian samples was identical. In the American sample, 22 WD chromosomes had a 5-marker haplotype matching the 6-marker haplotype "aA". Haplotypes aB and aC differ from aA at two marker loci. An additional 8 WD chromosomes contain a subset of 5-marker haplotypes which match these 6-marker haplotypes. An additional 9.4% of all WD chromosomes from the American sample had a 5 or 6-marker haplotype matching aD, aE, or aF. The most common haplotypes in the American sample account for approximately 50% of WD mutations. The remaining chromosomes in the American sample, as well as the Russian and Sicilian (not shown) sample, display very divergent haplotypes.

Experimental Discussion

A rapid physical mapping scheme was used to generate a dense collection of physically mapped microsatellite markers across the genetically defined Wilson's disease region. The method relies upon inter-Alu PCR amplification to selectively amplify human DNA from monochromosomal cell hybrids. The PCR product is then used to screen genomic YAC libraries for chromosome-specific clones (5, 15). Next, the method is used to amplify overlapping YAC clones (including chimeras) to screen cell-sorted, chromosome specific cosmid libraries. Individual "islands" of cosmid contigs are ordered by their pattern of hybridization to overlapping YAC clones and by STS mapping. This scheme circumvents the time consuming characterization of chimetic YAC clones and minimizes individual "walk" steps. The protocol constructs microsatellite marker maps at approximately 10-fold greater resolution than is possible by conventional genetic linkage analysis.

The utility of a high resolution microsatellite marker map is demonstrated by the analysis of 115 Wilson's disease families. In the Sardinia population, the disease locus is in significant LD with most markers spanning the genetically defined region, suggesting a possible Founder effect. In the more heterogeneous American families, the most significant LD is detected by marker loci D13S295 and D13S296.

A cDNA clone localized to a cosmid contig bracketed by these two markers provides strong evidence for LD. Amino acid homology and structural predictions indicate the cDNA encodes a copper-transporting ATPase with strong homology to the gene for Menkes disease (Mcl) (16), another copper metabolism disorder in humans. The C→A transversion alters a highly conserved histidine residue at the transduction domain and is a presumptive causal mutation. This evidence strongly suggests the cDNA clone (pWD) is the WD gene (11).

Haplotype analysis of the WD families from three disparate populations is likewise revealing. The most common haplotype in the American families detects 29% of all WD chromosomes. The CA transversion detected by the WD candidate gene is detected only on the aA/rA haplotype (11), supporting the assumption that the various WD haplotypes reflect independent disease mutations. This data indicates that approximately half of all WD mutations in the ethnically diverse American population (as well as the Russian population) will be rare, although there are examples of identical cystic fibrosis mutations on chromosomes with different haplotypes, and vice versa (17). A single haplotype accounts for approximately 65% of all WD chromosomes in Sardinia, but approximately 20% of mutations will predictably be rare even in this relatively homogeneous population. To the extent that these genetic haplotypes correlate with individual mutational events which cause Wilson's disease, this analysis provides a qualitative estimate of allelic heterogeneity of this disorder. The haplotype analysis presented in this study indicates that molecular diagnosis of Wilson's disease will be complicated, as is the current situation with cystic fibrosis (18).

Reference of the First Series of Experiments

1. Scheinberg, I. H., and Sternlieb, I., (1984) Wilson's disease. Volume XXIII ; Major Problems in Internal Medicine. WD Saunders Co. Lloyd H. Smith, Jr., ed.
2. Frydman, M., Bonne-Tamir, B., Farrer, L. A., et al. (1985). Proc. Natl. Acad. Sci. U.S.A., 82:1819–1821.
3. Farrer, L. A., Bowcock, A. M., Hebert, J. M., et al. (1991), Neurology, 41:992–999.
4. Albertsen, H. M., Abderrahim, H., Cann, H. M., Dausset, J., LePaslier, D., and D. Cohen. (1990), Proc. Natl. Acad. Sci. U.S.A., 87:4256–4260.
5. Fischer, S. G., Cayanis, E., Russo, J., Sunjevaric, I., Boukhgalter, B., Li, X.-L., Zhang, P., Rothstein, R., Yu, M.-T., Warburton, D., Edelman, I. S., and A. Efstratiadis. Assembly of ordered contigs from YAC-selected cosmids of human chromosome 13. Submitted.
6. Zhang, P., Schon, E. A., Fischer, S. C., Cayanis, E., Weiss, T., Kitler, S., and Bourne, P. E., submitted.
7. Petrukhin, K. E., Speer, M. C., Cayanis, E., Bonaldo, M. F., Tantravahi, U., Soares, M. B., Fischer, S. G., Warburton, D., Gilliam, T. C., and Ott, J. (1993) Genomics, 15:76–85.
8. Chakravarti, A., Buetow, K. H., Antonarakis, S. E., Waber, P. G., Boehm, C. D., and Kazazian, H. H., (1984), Am. J. Hum. Genet., 36:1239–1258.
9. Kerem, B., Rommens, J. M., Buchanan, J. A., Markiewicz, D., Cox, T .K., Chakravarti, A., Buchwald, M., and Tsui, L. C., (1989), Science, 245:1073–1080.
10. Nelson, D. L., Ledbetter, S. A., Corbo, L., Victoria, M. F., Ramirez-Solis, R., Webster, T. D., Ledbetter, D. H., and Caskey, C. T. (1989), Proc. Natl. Acad. Sci. U.S.A., 86:6686–6690.
11. Tanzi, R. E., Petrukhin, K., Chernov, I., Pellequer, J. L., Wasco, W., Ross, B., Romano, D., Brzustowicz, L. M., Devoto, M., Peppercorn, J., Bush, A., Sternlieb, I., Pirastu, M., St. George-Hyslop, P. H., Gusella, J. F., Evgrafov, O., Honig, B., Penchaszadeh, G. K., Edelman, I. S., Soares, M. B., Scheinberg, I. H., and T. C. Gilliam, submitted.
12. Schwartz, D., and Cantor, C. (1984), Cell, 37:67–75.
13. Warburton, D., Yu, M. T., Tantravahi, U., Lee, C., Cayanis, E., Russo, J., Fischer, S. (1993), Genomics, in press.
14. Weber, J. L. and Wong, C., (1993), Hum. Mol. Genet., 2:1123–1128 .
15. Chumakov, I., Rigault, P., Guillou, S., et al. (1992), Nature, 359:380–387.
16. Vulpe, C., Levinson, B., Whitney, S., Packman, S., and Gitschier, J. (1993) Nature Genetics, 3:7–13.
17. Mortal, N., Nunes, V., Casals, T., Chillon, M., Gimenez, J., Bertranpetit, J., and Estivill, X., (1993), Hum. Mol. Genet., 2:1015–1022.
18. Fujimura, F. K., (1991), Clin. Biochem., 24:353–361.
19. Orita, M., Iwahana, H. Kanazawa, H., Hayashi, K. & Sekiya, T. (1989) *Proc. Natl. Acad, Sci. USA,* 86, 2766–2770.
20. Orita, M., Suzuki, Y., Sekiya, T. & Hayashi, K. (1989) *Genomics* 5, 874–879.
21. Saiki, R. K., Gelfand, D. H., Stoffel, S., Scharf, S. J., Higuchi, R., Horn, G. T., Mullis, K. B. & Erlich, H. A. (1988) *Science* 239, 487–491.

22. Demers, D. B., Odelberg, S. J. & Fischer, L. M. (1990) *Nucleic Acids Res.* 18, 5575.
23. Dean, M., White, M. B., Amos, J., Gerrard, B., Stewart, C., Khaw, K. T. & Leppart, M. (1990) *Cell* 61, 863–870.
24. Ainsworth, P. J., Surh, L. C. & Coulter-Mackie, M. B. *Nucleic Acids Res.* 19, 405–406.
25. Suzuki, Y., Orita, M., Shiraishi, M., Hayashi, K. and Sekiya, T. (1990) *Ocogene* 5, 1037–1053.
26. Cawthon, R. M., Weiss, R., Xu, G., Viskochil, D., Culver, M., Stevens, J., Robertson, M., Dunn, D., Gesteland, R., O'Connell, P. & White, R. (1990) *Cell* 62, 193–201.

Second series of Experiments

Wilson's disease (WD) is an autosomal recessive disorder characterized by the toxic accumulation of copper in a number of organs, particularly the liver and brain. Genetic linkage studies have mapped the disease gene to 13q14.3. A partial cDNA clone (pWD) is described which maps to this region. Sequence analysis indicates the candidate gene is a copper-transporting ATPase with 62% amino acid identity to Mc1, the gene responsible for the X-linked copper metabolism disorder, Menkes disease. The predicted functional properties of the pWD gene together with its strong homology to Mc1, genetic mapping data, and population genetic evidence for identification of a disease-specific mutation, strongly imply that pWD is the Wilson's disease gene.

Wilson's disease (WD) is an autosomal recessive disorder of copper metabolism with a world-wide prevalence of 30 per million and a corresponding carrier frequency of 1 in 90. Biochemically, it is characterized by abnormally high concentrations of copper particularly in the liver and brain, and deficiency of the plasma copper-protein, ceruloplasmin. Affected individuals initially accumulate vast increases in hepatic copper-leading to the development of acute or chronic liver disease. Cooper subsequently also deposits in the brain, where it causes profound psychiatric and neurological symptoms that are the direct consequences of copper's toxicity. The disease is always fatal if untreated but pharmacologic removal of the excess copper can be dramatically effective therapy for patients with hepatic or cerebral symptomatology (1). X-linked Menkes' disease is likewise a lethal disorder of copper metabolism (2), but one in which deficiency of copper appears to be the fundamental cause of diverse clinical abnormalities resulting from the reduced activity of essential copper-dependent proteins. The principal pathology of both Wilson's disease and Menkes' disease appears to be a defective copper transport mechanism. Recently, several X-chromosome translocations associates with Menkes' disease were characterized to reveal the apparent disruption of a copper-transporting ATPase (Mc1) (3). The Mc1 gene is the first reported eukaryotic copper-transporter molecule and a convincing candidate for the Menkes' disease gene.

In 1985, genetic linkage studies showed that the Wilson's disease locus segregates with the red cell enzyme esterase-D (ESD) on chromosome 13 (4), and subsequent studies refined the disease locus considerably (5). Recently, the disease region was cloned microsatellite markers were identified and ordered across the locus, and haplotype and linkage disequilibrium analysis was performed on 115 Wilson's disease families. A novel cDNA clone was mapped to the genetic interval demonstrating the strongest disequilibrium to the WD locus (6). We now report the characterization of this cDNA clone and of an associated mutation in Wilson's disease patients. We propose that pWD encodes the normal protein that prevents development of Wilson's disease.

Isolation of cDNA Clones

The 3.5 kb pWD02 cDNA clone was identified by hybridization of an oligo(dT)-primed brain cDNA library with a degenerate oligonucleotide to a novel heavy metal binding site situated on the A-β protein of the amyloid β-protein precursor (7). Preliminary evidence indicated that this clone mapped to chromosome 13q14 (unpublished observation) and DNA sequence of a 500 bp subclone revealed strong amino acid sequence homology to Mc1, the putative Menkes' disease gene (3). The cDNA clone was physically mapped to the genetically defined WD gene region (6). These data strongly implicated pWD02 as a candidate for the WD gene.

Figure 3:
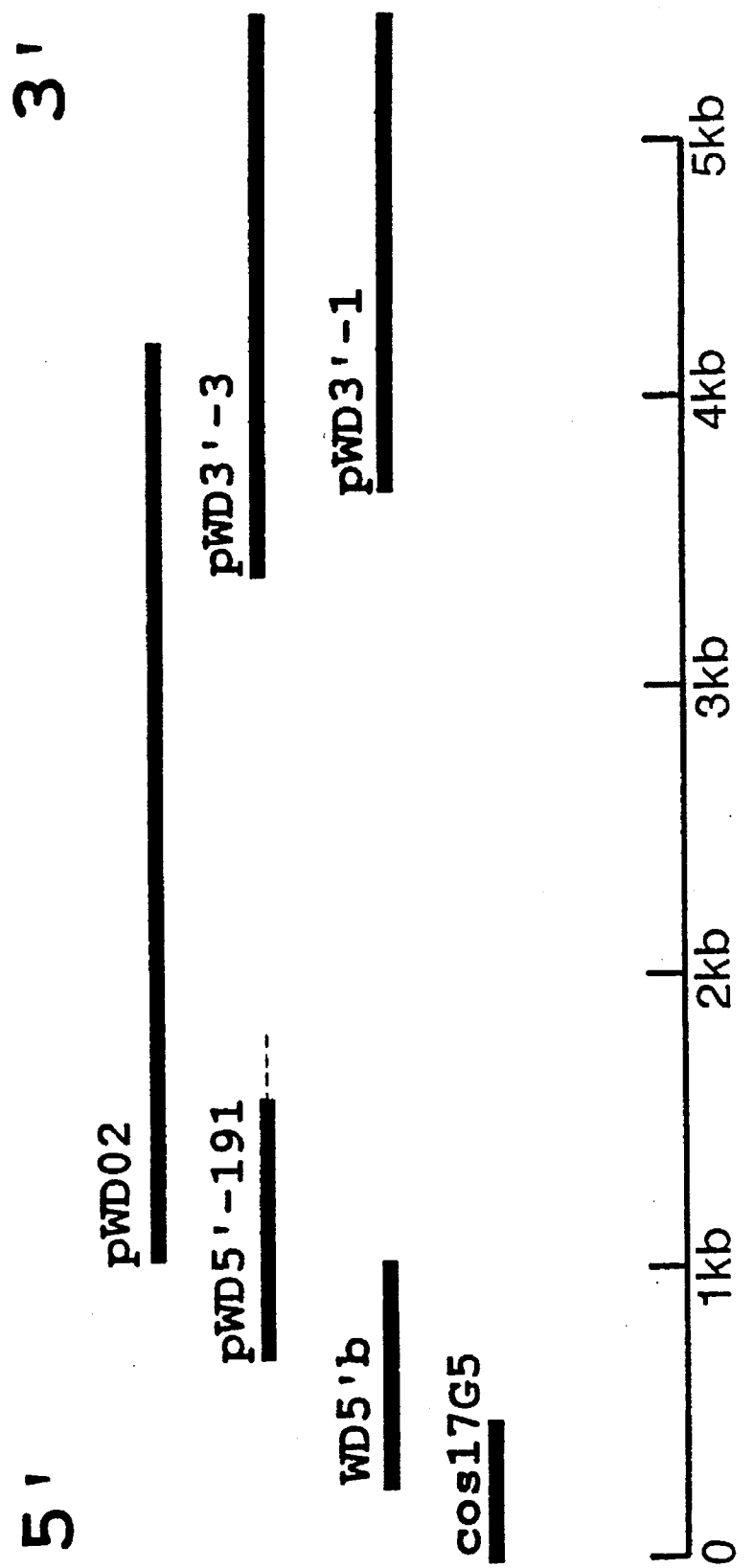
FIG. 3 Extension of the pWD02 cDNA clone. See text and (9 of the second series of experiments).

Clone pWD02 contained 3477 bp of DNA which was subsequently shown to include 2491 bp of coding sequence and 985 bp of 3' untranslated RNA. An oligonucleotide was synthesized from the 3'-most end of pWD02 and used to screen a "normalized" brain cDNA library (8). A 2.1 kb cDNA clone, pWD3'-3 and a 1.5 kb clone, pWD3'-1 were identified (FIG. 3). Both clones contained two AATAAA polyadenylation consensus sites and poly A tracts. Additional sequence at the 5'-end of the pWD gene was identified by screening 5 cDNA libraries (9) in conjunction with genomic DNA sequencing from homologous cosmid clones. FIG. 1 illustrates the 5' extension of the clone through identification of 197 bp of new sequence from pWD5'-191, 520 base pairs from the PCR amplification product WD5'b, and 243 base pairs from a homologous cosmid clone (17G5). The 5'-terminus of the gene has not yet been identified. In total, 5422 base pairs of the pWD gene have been cloned which encode 1110 amino acids and 2042 base pairs of 3' untranslated region (10).

Expression of the pWD Gene

Figure 4:
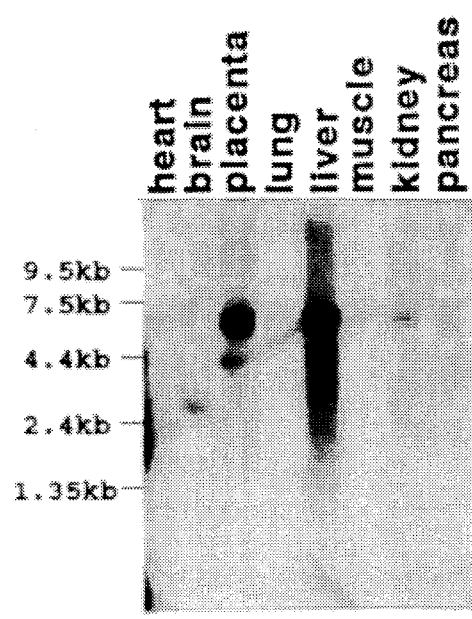
FIG. 4 Northern blot analysis of pWD02 cDNA clone. The Northern blot was purchased from Clonetech and hybridized with radiolabeled pWD02 DNA probe. Poly(a)+ RNA from various tissues is indicated at the top of each well.
Figure 7:
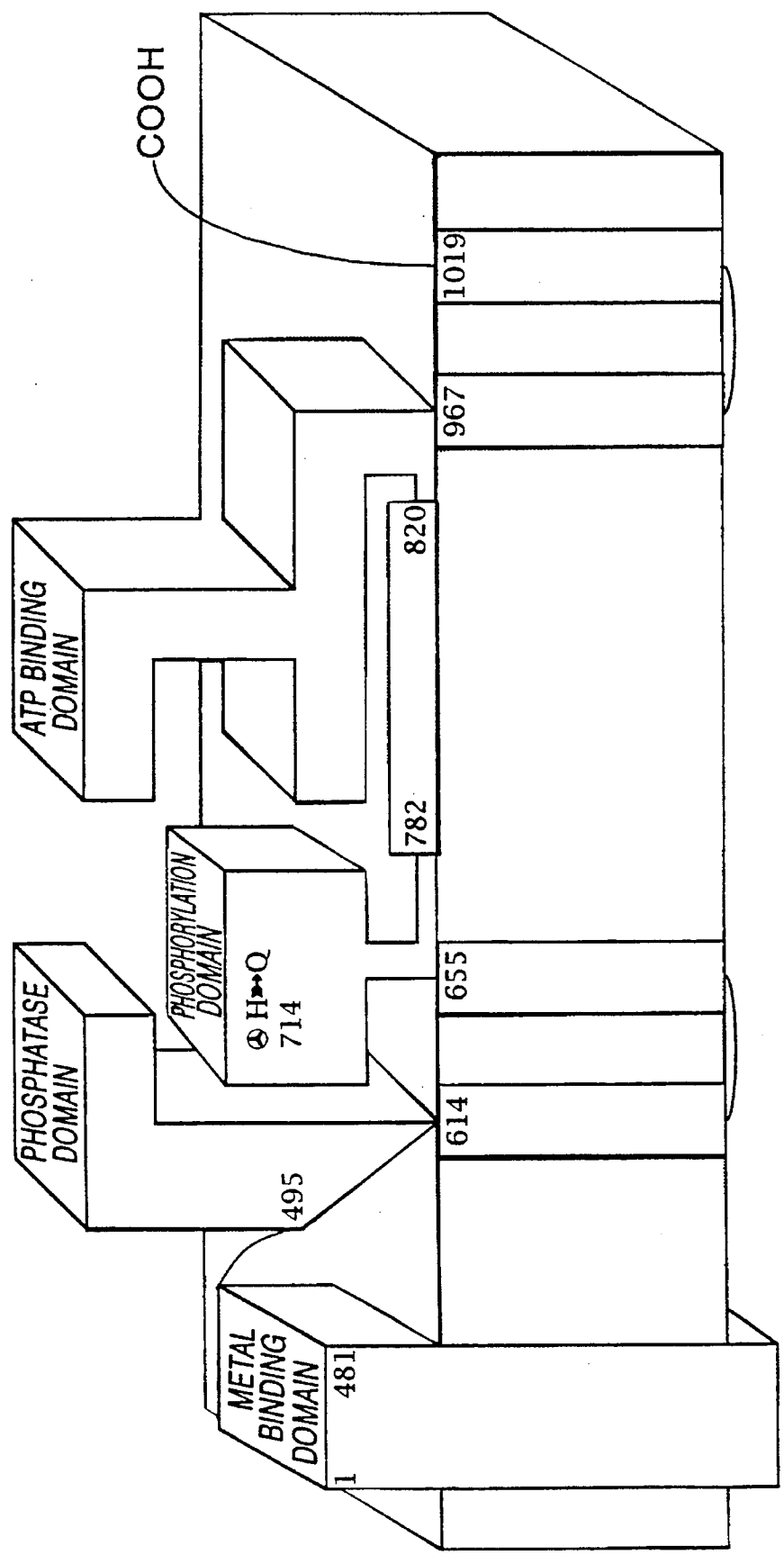
FIG. 7 Model of the architecture of the pWD protein. The model is based upon the observed consensus sequences (multi-alignment) and on the secondary structure predictions (18 of the second series of experiments). There are four transmembrane helices (see text). The rest of the molecule is intracellular since typical intracellular domains have been predicted (ATP binding site, phosphorylation site, etc.) except for a potential metal binding transmembrane domain. This model represents the expected interaction between the nucleotide binding domain, phosphorylation site and phosphatase/transduction domain.

Hybridization of clone pWD02 to a Northern blot (Clontech) containing polyA+ RNA showed expression of the WD gene in all tissues where it was tested, including heart, brain, placenta, lung, liver, skeletal muscle, kidney and pancreas. Expression was most pronounced in the liver and placenta (FIG. 4). The transcript size is estimated as approximately 5.9 kb. To date, applicants have not been successful in isolating intact RNA for Northern blot analysis from WD liver transplant samples or from WD liver biopsies. Applicants have, however, detected pWD gene expression by reverse transcriptase PCR of both WD liver biopsy RNA and WD lymphoblast RNA (data not shown).

Sequence Analysis of DWD

Both strands of the pWD cDNA were sequenced in at least 2 cDNA clones, and for much of the gene, multiple cDNA clones and/or genomic DNA was sequenced (11). One open reading frame of 3330 bp encoding 1110 amino acids is shown in FIGS. 5A–5H. Two poly A consensus motifs (AATAAA) are detected (4903–4908, 5392–5397), and a poly A tract is shown at the 3' terminus. The 5' terminus is not yet cloned as indicated by the open reading frame continuing to the first codon and the absence of an initiation codon and consensus sequence. The partial cDNA spans approximately 80 kb of genomic DNA (data not shown). Preliminary data indicates a total of 19 intron/exon junctions.

Searches of protein databases (12) revealed a strong homology with the ATPase family including the Mc1 protein (Menkes disease) (3), Enterococcus hirae Cu++ exporting ATPase (13) and prokaryotic cadmium transporter (14). The pWD protein has a metal binding site domain and three cytoplasmic ATPase domains (ATP binding domain, phosphorylation domain, and phosphatase domain). The last three domains are characteristic of P-type, or transducing, ATPases (15, 16). In addition to ATPase cytoplasmic domains, pWD appears to have a number of transmembrane helices. The presence of all these features suggest that the pWD protein is a metal transporting ATPase.

Metal Binding Site (1–481)

Figure 8A:
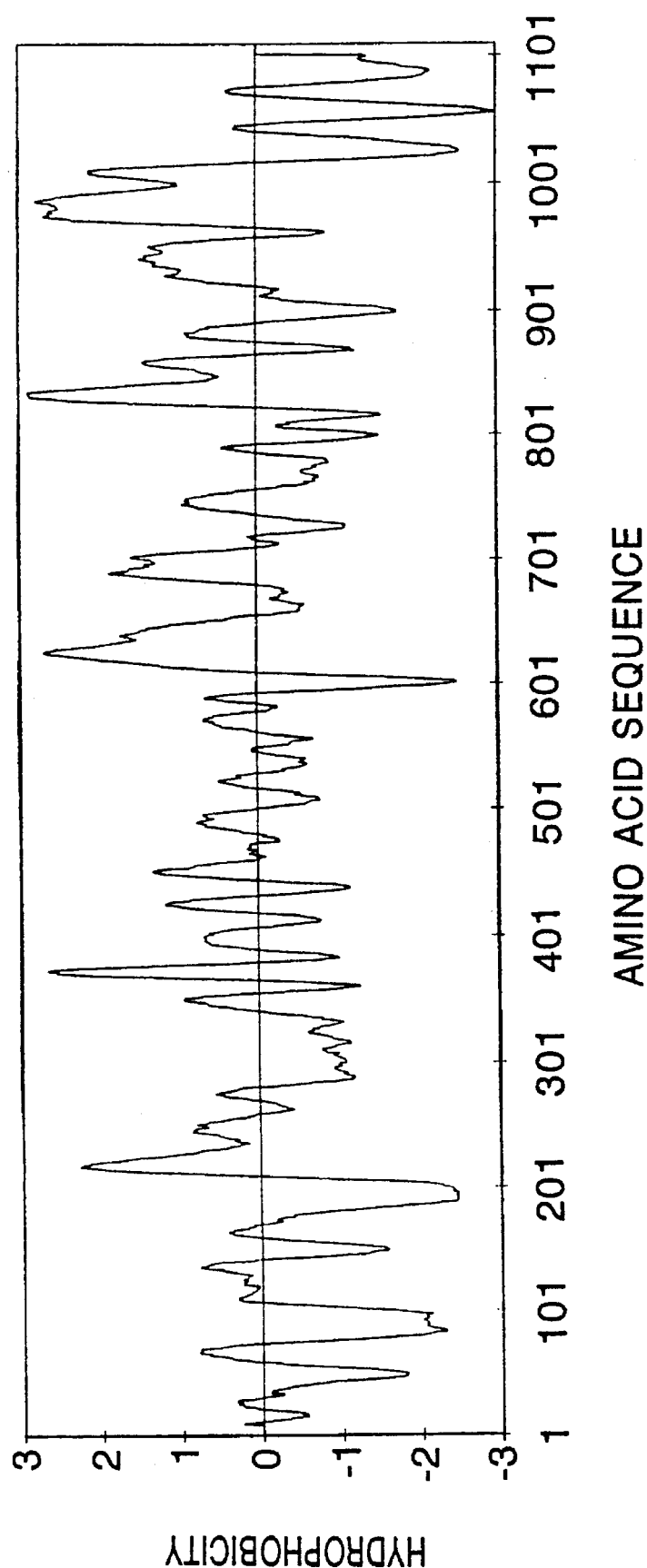
FIG. 8A and 8B Hydrophobicity and charge profiles of pWD.
Figure 8B:
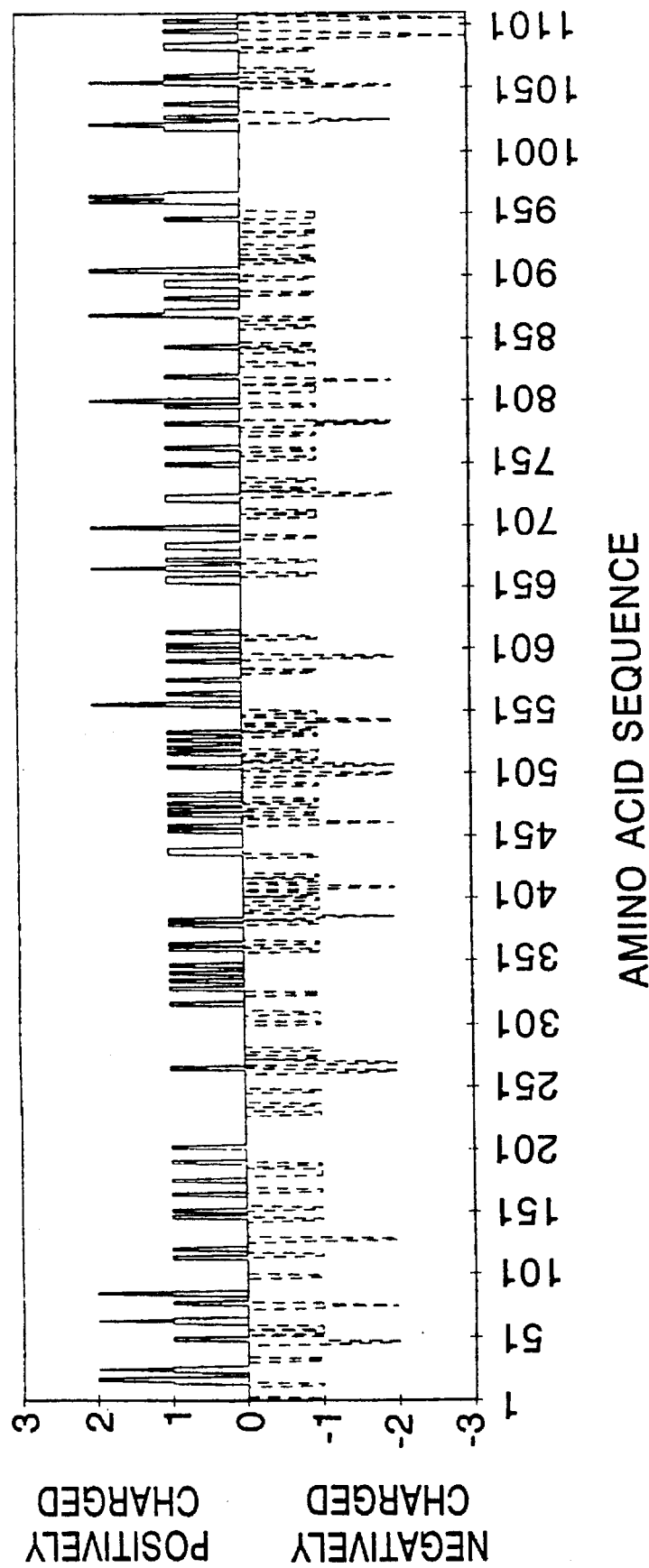

There are five metal binding regions, each about 50 residues long which contain a GXXCXXC (SEQ ID No. 20) motif (FIGS. 6A–6D 7). This motif has been found in other proteins that bind or transport metals (13, 16). The five regions are highly homologous, however, the sequences connecting them are quite different. The presence of five metal binding sites in pWD and six in Mc1 is in contrast to the presence of one or two such motifs in other published sequences (17). FIG. 8A presents the hydrophobicity profile of pWD and FIG. 8B contains a profile of positive charges and few negative charges. There is a hydrophobic peak around the third metal binding site (210–258) which corresponds to a region of no positive charges and few negative charges. Moreover, there are a number of portable extracellular N-glycosylation sites between the first, second, third, and fourth metal binding sits (96–99, 146–149, 290–293). This evidence suggests that the metal binding domain contains transmembrane regions and may be the location of cation transport.

Phosphorylation Domain (656–782)

This domain contains an invariant aspartic acid and DKTGTIT sequence found in P-type ATPases (FIGS. 6A–6D; 16). In pWD, Ile is replaced by Leu. In calcium ATPase the conserved aspartic aid residue is believed to be phosphorylated as an integral part of the cation transport cycle. The ATP driven reaction to form phosphoenzyme at this site is central to the mechanism of energy transduction by ATPases. This domain contains the mutated amino acid found in a significant proportion of the Wilson's disease patients.

ATP Binding Domain (820–967)

This domain extends between the putative 4th and 5th transmembrane helices. It contains a lysine (820) followed by a glycine which may be related to an FITC binding lysine in other ATPases (16). The domain ends with a hinge region containing the consensus sequence GDGXNDXPL (SEQ ID No. 21) (FIG. 6; 16). Secondary structure prediction algorithms (18) assign a repeating ($\alpha\beta$) motif (19) which is found in ATP binding domains in proteins whose three dimensional structure is known (20).

Transmembrane sediments

Five hydrophobic segments can be clearly identified in the pWD sequence. Of these, two (614–655, 967–1019) correspond to regions with no positive and negative charges. Based on their length, each is assumed to contain a pair of transmembrane helices. The first transmembrane helix contains a cation binding site composed of two cystsines flanking a proline residue. This conserved proline may be involved in the transduction process in $Ca^{++}$ ATPases (21).

The peaks (823–864, 920–958) are unlikely to be transmembrane because they fall in the cytoplasmic ATPase domain. The peak (681–710) is not assigned to a transmembrane helix because it is not long enough to go through the membrane twice. Applicants have excluded the possibility that the peaks at (6141–655) and (681–710) constitute a transmembrane pair because the phosphorylation site at 672 must be cytoplasmic. Based on hydrophobic moment calculation (22), applicants can identify a long amphophilic helix (78214 820) but it is unclear whether it is a transmembrane helix.

The single most striking feature of the pWD protein is a 62% identity and 76% amino acid homology with the Mc1 protein of Menkes disease. The overall design of the two proteins is likewise strikingly similar, each with the requisite transducing ATPase moieties and multiple copper binding sites.

Applicants' sequence analysis has revealed remarkable structural similarities in two genes each of which prevents a unique lethal disorder of copper transport. The pWD protein appears to differ from the Mc1 protein in several ways. First, there are four segments of the Mc1 gene which are missing in the pWD gene in addition to 6 short segments which are unique to the pWD gene (FIGS. 5A–5H). The largest missing segment corresponds to the fourth transmembrane helix in Mc1 and another deletion to the fifth transmembrane helix. These deletions imply a different pattern in the transmembrane segments between the two proteins. In the Menkes protein, there is a potential extracellular region between two consecutive transmembrane helices (including basic residues) whereas the sequences between transmembrane helices in the pWD protein are quite short and have no predicted extracellular region. In addition, no stalk is detected in the pWD protein, unlike the Mc1 protein. Moreover, in the Mc1 protein, eleven Asn-glycosylation sites are predicted by the program MOTIFS (23) in contrast to four in the pWD protein.

The pWD protein has five predicted metal binding sites as compared to six in Mc1. There may be a sixth site at the 5'-terminus of the pWD gene which is not yet cloned. In contrast to the suggestion made for the Menkes protein (3) applicants have postulated that the metal binding domain for both pWD and Mc1 contain a transmembrane region, which may be involved in the energy-linked translocation of copper.

Detection of a Disease-Specific Mutation

Applicants have shown that the most common "WD haplotype" (25% of all WD chromosomes) in the Russian and U.S. samples occurs in only ~2% of "normal" chromosomes (6). An individual homozygous for this haplotype was DNA sequenced (24) and compared to the sequence generated from the pWD cDNA clones. A CA transversation (2142) was detected which changes a histidine residue to glutamine (FIGS. 6A–6D, 9) (25). DNA sequence was determined for both strands across this region in 8 WD families (6 American and 2 Russian) where one or two affected children were homozygous for the common haplotype. In all 8 families, both parents were shown to be heterozygous C/A, while all 9 affected children were homozygous A/A (data not shown). Table I shows the microsatellite marker haplotypes at nine loci spanning the Wilson's disease locus (26). The aA haplotypes displayed in Table I are minor variations of the pattern (- - 2 5 9 14 4 3 - -) as described (6). Applicants have shown that WD chromosomes bearing the closely related aB (- - 15 10 14 4 3 - -) haplotype (6) encode the normal histidine residue, as do all other WD and normal haplotypes tested (data not shown). In all, 22 of 22 WD chromosomes bearing the most common WD haplotype carry the $A^{2142}$ residue. Only 2 of 109 normal chromosomes identified from the Wilson's disease families display this haplotype (6). These two individuals and their parents were sequences to reveal a $C^{2142}$ as shown in Table I. In addition, 100 presumptive normal (not haplotyped) chromosomes were DNA sequenced from unrelated individuals (non-Wilson's disease families) and all encoded the normal $C^{2142}$ residue. Thus, the C→A transversion appears to be a disease-specific mutation as opposed to a tightly associated polymorphism.

Heavy metal ion-transporting ATPases are characterized by a conserved CPC sequence located 41 amino acids downstream of the DKTG phosphorylation site. These sequences may play a role in cation binding and transport across the membrane (27). The histidine to glutamine transversion at his714 residues 39 amino acids C-terminal to the DKTG phosphorylation domain. The histidine and adjacent proline residues are highly conserved among heavy metal-transporting ATPases (FIGS. 6A–6D, 9) suggesting that disruption of the histidine residue would be critical to the ability of the protein to transfer copper ions across the membrane into the luminal space. It is proposed that mutational replacement of the highly conserved histidine residue with glutamine accounts for illness from copper toxicity in 25%–30% of WD patients from the U.S. and Russian clinical samples. It is further proposed that the S/X/H/P.L-I/G-A/X/A/I motif is essential to ATPase function as indicated by the pWD mutation.

Several lines of evidence make it very likely that pWD is the gene responsible for Wilson's disease: (i) the gene maps to the genetically defined disease gene region and demonstrates strong linkage disequilibrium with the disease phenotype (6); (ii) the derived amino acid sequence predicts a protein with copper-transporting ATPase activity. Loss of this function is consistent with the disease phenotype; (iii) the derived amino acid sequence is 62% identical and 76% homologous to the Menkes disease gene, Mc1. Much evidence suggests that both Menkes disease and Wilson's disease result from improper cellular transport of copper; (iv) a CA transversion at position 2142 disrupts a highly conserved histidine residue believed to be involved in cat-ion-coordination and transport across the membrane. The transversion appears to be disease-specific; and (v) the pWD transcript is heavily expressed in liver tissue.

The similarities between the two most prominent disorders of copper metabolism in humans has led several investigators to speculate that the disorders will share a common molecular basis. Most recently, the discovery of a putative copper-transporting ATPase as the protein which mutates to cause Menkes disease prompted investigators to predict that Wilson's disease would result from mutation of a similar protein (3). The accuracy of this prediction would seem to be borne out by the structure and predicted function of pWD. The differences in the pWD and Mc1 proteins may reflect the opposite life-preserving role each plays in the metabolism of copper. Mc1 appears to regulate the distribution of dietary copper to sites of copper-dependent protein synthesis. Several investigators have suggested that Mc1 acts principally at the basal-lateral surface of intestinal mucosal cells where its role is to transport dietary copper into the blood stream. Since pWD has all the characteristics of a copper transporting ATPase, it seems reasonable that the protein may reside on the apical pole of hepatocytes and functions to export excess copper from the liver via the bile canaliculi. Although compatible with the structure and predicted function of pWD, this mechanism leaves unexplained the significance of the deficiency of ceruloplasmin, which is seen in 95% of patients with Wilson's disease (27).

TABLE III

|  | Locus D13S | | | | | | | | | Disease | |
|  | 294 | 295 | 301 | 296 | 133 | 297 | 298 | 299 | 300 | Status | Genotype |
|---|---|---|---|---|---|---|---|---|---|---|---|
| aA | 13 | 2 | 5 | 9 | 14 | 4 | 3 | 16 | 2 | aWD | A |
|  | 13 | 2 | 5 | 9 | 14 | 4 | 3 | 16 | 3 | aWD | A |
|  | 4 | 2 | 5 | 9 | 14 | 4 | 3 | 16 | 2 | aWD | A |
|  | 3 | 2 | 5 | 9 | 14 | 4 | 3 | 16 | 3 | aWD | A |
|  | 13 | 2 | 5 | 8 | 14 | 4 | 3 | 16 | 2 | aWD | A |
|  | 13 | 2 | 5 | 9 | 14 | 4 | 3 | 16 | 2 | aWD | A |
|  | 4/5 | 2 | 5 | 9 | 14 | 4 | 3 | 16 | 2 | aWD | A |
|  | 13 | 2 | 5 | 9 | 14 | 4 | 3 | 16 | 2 | aWD | A |
|  | 13 | 2 | 5 | 9 | 14 | 4 | 3 | 16 | 2/3 | aWD | A |
|  | 6 | 2 | 5 | 9 | 14 | 4 | — | 16 | 2 | aWD | A |
|  | 4 | 1/2 | 5 | 9 | 14 | 4 | 3 | 16 | 2 | aWD | A |
|  | 7 | 2 | 5 | 9 | 14 | 4 | 3 | 16 | 2 | rWD | A |
|  | 4 | 2 | 5 | 9 | 13 | 4 | 3 | 16 | 2 | aWD | A |
|  | 13 | 2 | 10 | 9 | 14 | 4 | 3 | 16 | 2 | aWD | A |
|  | 13 | 2 | 5 | 9 | 3/14 | 4 | 1 | 16 | 2/3 | aWD | A |
|  | — | 1 | 5 | — | 14 | 4 | 3 | — | — | aWD | A |
|  | 4 | 1 | 5 | 9 | 14 | 4 | 3 | 16 | 2 | rWD | A |
|  | 4 | 1 | 5 | 9 | 14 | 4 | 3 | 16 | 2 | rWD | A |
|  | 6 | 1 | 5 | 9 | 14 | 4 | 3 | 16 | 2 | rWD | A |
|  | — | 3 | 5 | 9 | 14 | 4 | 3 | — | 2 | aWD | A |
|  | 4/5 | 3 | 5 | 9 | 14 | 4 | 3 | 16 | 2 | aWD | A |
|  | 4 | 3 | 5 | 9 | 14 | 4 | 3 | 16 | 2 | rWD | A |
|  | 4 | 3 | 5 | 9 | 14 | 1 | 4 | 16 | 3 | aN | C |
|  | 6 | 4 | 5 | 9 | 14 | 4 | 3 | 16 | 2 | aN | C |
| aB | — | — | 5 | 10 | 14 | 4 | 3 | 16 | 1 | aWD | C |
|  | — | — | 6 | 10 | 14 | 4 | 3 | 16 | 9 | aWD | C |
|  | 6 | 1 | 6 | 10 | 14 | 4 | 3 | 16 | 9 | aWD | C |
|  | 4 | 1 | 5/6 | 10 | 14 | 4 | 3 | 7 | 2 | aWD | C |
| aC | 11 | 1 | 7 | 10 | 14 | 3 | 7 | 4 | 3 | aWD | C |

Table III Correlation of haplotypes with the putative disease-specific mutation. Genotypes are shown for each of 9 microsatellite markers spanning the WD gene region (6). The WD candidate gene maps between loci D13S295 and D13S296, on the same cosmid clone as locus D13S301 (26). "aWD" refers to affected individuals from the American sample, and "rWD" to affected individuals from the Russian sample.

REFERENCES AND NOTES OF THE SECOND SERIES OF EXPERIMENTS

1. Scheinberg, I. H. and Sternlieb, I., (1984) Wilson's Disease. Volume XXIII; Major Problems in Internal Medicine, W. B. Saunders Co., Lloyd H. Smith, Jr., ed.
2. Menkes, J. H., Alter, M., Steigleder, G. K., Weakley, D. R. and Sung, J. H., (1962), Pediatrics, 29:764–779.
3. Vulpe, C., Levinson, B., Whitney, S., Packman, S. and Gitschier, J., (1993), Nature Genetics, 3:7, Chelly, J., et al., ibid, 3:14, Mercer, J. F. B., et al., ibid 3:20.
4. Frydman, M., Bonne-Tamir, B., Farrer, L. A., et al., (1985) Proc. Natl. Acad. Sci. U.S.A., 82:1819.
5. Bonne-Tamir, B., Farrer, L. A., Frydman, M., Kannaane, L. H., (198) Genet. Epidemiol., 3:201; Bowcock, A. M., Farrer, L. A., Cavalli-Sforza, L. L., et al., (1987), 41:27; Farrer, L. A., Bowcock, A. M. and Herbert, J. M., et al. (1991).
6. Petrukhin, et al., submitted.
7. The DNA sequence of the oligonucleotide is: GGC TAC CAG GTG CAC CAC CAG AAG CTG GTG TTC TTC GCC GAG GAC GTG. A description of the novel binding site is described in Al Bush, et al., in press.
8. Adams, M. D., et al. (1993) Nature Genetics, 4:373–380.
9. Two liver/spleen cDNA libraries were constructed from 20 week post-conceptus fetal material. The libraries were constructed in pT7T3 vector (Pharmacia) modified to contain a Pac I site. The normalized infant brain cDNA library was constructed from a three month post natal infant in the LAFMID BA vector using the cloning sites HindIII and Not I. The directionally cloned infant brain cDNA library was normalized by a kinetic approach involving priming of single-stranded circles with a Not I-(dT) 15 oligonucleotide and controlled extensions (150–200 nt) with Klenow enzyme in the presence of dNTPs and ddNTPs. After purification of the partial duplexes over hydroxyapatite (HAP), melting and reannealing to a moderate Cot, unhybridized (normalized) single-stranded circles were purified over HAP and electroporated into bacteria. The oligo(dT)-primed brain cDNA library used to isolate pWD02 and a Clonetech fetal liver cDNA library were likewise screened.
10. The pWD02 cDNA clone was used to screen a 16,896 clone, chromosome 13-specific cosmid library (Brown, N., Longmire, J. and Deaven, L.). Eleven cosmid clones were identified. Two "walk-steps" were performed using the riboprobe labelling method (6) which extended the cosmid contig to a total of 16 cosmids. A 5' pWD02 oligonucleotide (961–980) was used to prime the DNA synthesis (10) of 50 additional bp of coding sequence from homologous cosmid clones (17G5, 15F1), and a 100 bp PCR fragment including this new sequence was synthesized. 5 cDNA libraries were screened with PCR primers for this fragment (9), two fetal liver/spleen libraries were positive, and one positive clone (pWD5'-191) was identified by screening the libraries with radiolabelled 110 bp fragment. pWD5'-191 was incompletely spliced and contained only 197 bp of new sequence. 5' oligonucleotides were generated (765–789) and used in conjunction with vector primers to amplify the two fetal liver/spleen cDNA libraries. A 550 bp PCR fragment (WD5'b) (253–278), applicants sequenced cosmid 17G5 and obtained 243 bp of additional sequence(FIG. 1). The entire 5414 bp of pWD cDNA is localized to two overlapping clones which span approximately 80 kb.
11. DNA sequencing was performed using the Taw DyeDeoxy Terminator Cycle Sequencing Kit (ABI) as recommended by the supplier. The reactions were analyzed on a ABI model 373A automated sequencer. The forward and reverse primers of pUC18 were used to prime the synthesis of about 300 bp from either end of pWD02. A new set of oligonucleotide primers were generated from the 3'-most end of each new extension and used to prime the next extension as well as to re-sequence the previous sequence for verification. All primers were used in subsequent reactions to sequence first strand cDNA generated from WD polyA+RNA.
12. A sequence homology search with the WD protein sequence was performed using the BLAST Network Service (Altschul, S. F., Gish, W., Miller, W., Myers, E. W. and Lipman, D. J., (1990), J. Mol. Biol., 215:403.
13. Oedermatt, A., Suter, H., Kraps, R. and Solioz, M., J. Biol. Chem., 268:12775–12779.
14. Ivy, D. M., et al. (1992) J. Bacteriol., 174:4878–4882.
15. Silver, S. and Walderhaug, M., (1992), Microbiol. Rev., 56:195.
16. Silver, S., Nucifora, G., Chu, L. and Misra, T. K., (1989), Trands Biochem. Sci., 14:76–80.
17. Nucifora, G., Chu, L., Misra, T. K. and Silver, S., (1989), Proc. Natl. Acad. Sci. U.S.A., 86:3544–3548.
18. Transmembrane segments have been identified with a hydrophobicity plot and a profile of charged amino acids. The former was based on the hydrophobicity scale of Kyte and Doolittle (28) using a window length of 19 residues. The charge profile for positive charges is generated by assigning a value of +3 to all arginines and lysines, and zero for all other residues. A window of three amino acids is used with the value plotted for residue is corresponding to the average of i−1, i, and i+1. An identical procedure is sued for negative charges except that a value of −3 is now assigned to glutamic and aspartic acids. The amphipathic profile of pWD was calculated by the PREDITOP software (29) according to the hydrophobic moment of Eisenberg, et al., (22) and the hydrophobicity scale of Cornette et al., (30). Secondary structure prediction was carried out with the GCC package using both the Chou-Fasimer (31) and Carnier (32) algorithms.
19. $\alpha\beta$ nucleotide binding domain: B1$\alpha$1B2 $\alpha$2B3$\alpha$3: 825–831; 836–855; 858–883; 885–901; 906–911; 919–929.
20. Branden, C. and Tooze, J., (1991), Introduction to protein structure (Garland Publishing, Inc. New York.
21. Vilsen, B., Andersen, J. P., Clarke, D. M. and Macennan, D. H., (1989), J. Biol. Chem., 264:21024–21030.
22. Eisenberg, D., Weiss, R. M. and Terwilliger, T. C., (1984), Proc. Natl. Acad. Sci. U.S.A., 81:140–144.
23. Devereau, J., Haeberli, P. and Smithies, O., (1984), Nucl. Acid. Res., 12:387–395.
24. Total RNA was extracted by the guanidinium thiocyanate-phenol-chloroform method (Chomczunsky, PJ. and Sachi, N., Anal. Biochem., (1987), 162:156–159). Poly (A)+RNA was isolated (Maniatis, T., Fritsch, E. F. and Sambrook, J., (1989) A laboratory manual. Cold Spring Harbor, Cold Spring Harbor Laboratories) from lymphoblast cell cultures, followed by synthesis of first strand cNDA using reverse transcriptase (Clontech RT-PCR kit), and PCR amplification using nested oligonucleotide primers obtained from the sequence of the "normal" cDNA strand. PCR amplification products were electrophoresed through 1.5% agarose (low melting point, Boehringer) and the DNA fragment was recovered after melting the agarose and passing through a Quiagen tip 20 (Quiagen Inc.). DNA sequence was verified for every base pair by a second, independent PCR amplification and sequencing. Portion of pWD gene sequences were determined by PCR amplification of genomic exonic sequence using oligonucleotide primers for intronic sequence spaced about 50 bp from the exon/intron junction. The pWD cDNA was divided into 14 overlapping regions of 200–500 bp in size. Not all 14 regions were successfully amplified in the lymphoblast samples, possibly due to low level of WD mRNA expression.

25. The only other sequence difference detected was a AG transversion at 1565 giving rise to a conservative lysine to arginine transition. The polymorphism showed allelic association with the WD locus, but was detected as a homozygote two normal individuals (data not shown). It is thus unlikely that this transversion is a causal mutation. This polymorphism was detected by isolation of poly(A)+ RNA from a WD liver biopsy sample, followed by first strand cDNA synthesis (24). The region from nucleotide 882 to 4359 was sequenced using nested primers constructed from the synthesis of the pWD02 cDNA clone (11).

26. The pWD gene was physically mapped to a group of overlapping cosmid clones bracketed by the adjacent microsatellite markers D13S295 and D13S296. These two markers provided the strongest evidence for linkage disequilibrium in a study of 115WD families from several diverse populations. Applicants have shown by pulsed filed gel electrophoresis that pWD resides less than 80 kb from D13S296 (unpublished observation). pWD is located on the same cosmid clone as D13S301 (6).

27. Gibbs, K., Walshe, J. M., (1979), Quart. J. Med., Sass-Kortsak, A, Bearn, A. G., in The Metabolic Basis of Inherited Disease, 4th ed. Ed. by J. B. Stanbury, et al., McGraw-Hill, New York, 1978, pp. 1098–1126; Scheinberg, I. H., Sternlieb, I., Wilson's Disease, Saunders, W. B., Philadelphia, 1984, page 19.

28. Kyte, J., Doolittle, R. F., (1982), J. Mol. Biol., 157:105–132.

29. Pellequer, J-L., Westhof, E., Van Regenmortal, M. H. V., (1993), Immunol. Lett., 36:83–100.

30. Cornette, J. L., et al. (1987), J. Mol. Biol., 195:659–685.

31. Chou, P. Y., Fasman, G. D., (1974), Biochemistry, 13:222–245.

32. Garnier, J., Osguthorpe, D. J., Robson, B., (1978), J. Mol. Biol., 120:97–120.

33. 500 ng of genomic DNA was amplified using the primers flanking the exon containing the CA transversion. A 337 bp PCR product was purified as described (24) and sequenced using the same primers used for amplification. The sequence of the primers is as follows: 3348=CAG CTA CCA GAG AAG GAC ATG G (SEQ ID No. 22); 3349=AFT TCT GCC TCA GGA GTG TGA C. DNA sequence was analyzed with an ABI model 373A automated sequencer. Heterozygotes were reliably detected by manual inspection of characteristic "double peaks" at nucleotide 2142.

34. Mc1 refers to the putative disease gene for Menkes disease (3). CopA is a copper-transporting ATPase from Enterococcus hirai (13). Fix1 is an unknown cation-transporting ATPase from Rhizobium meliloti (Kahn, D., et al. (1989) J. Bact., 171:929). CadA is a cadmium afflux ATPase from *Staphylococcus aureus* (17).

---

What is claimed is:

1. An isolated, nucleic acid molecule encoding a human metal transporting ATPase having the amino acid sequence as shown in FIG. 5.
2. A DNA molecule of claim 1.
3. A cDNA molecule of claim 2.
4. A genomic DNA molecule of claim 2.
5. An RNA molecule of claim 1.
6. An isolated nucleic acid molecule of claim 3 operatively linked to a promoter of RNA transcription.
7. A vector which comprises the nucleic acid molecule of either claims 2 or 6.
8. A vector of claim 7, wherein the vector is a plasmid.
9. The vector of claim 8 designated pWD5'-191 (ATCC Accession No. 75544).
10. The vector of claim 8 designated pWD3'-1 (ATCC Accession No. 75546).
11. The vector of claim 8 designated pWD3'-3 (ATCC Accession No. 75545).
12. (Amended) The vector of claim 8 designated pWD02 (ATCC Accession No. 75543).

* * * * *